(12) United States Patent
Palmaz et al.

(10) Patent No.: US 7,195,641 B2
(45) Date of Patent: Mar. 27, 2007

(54) VALVULAR PROSTHESES HAVING METAL OR PSEUDOMETALLIC CONSTRUCTION AND METHODS OF MANUFACTURE

(75) Inventors: Julio C. Palmaz, San Antonio, TX (US); Eugene A. Sprague, San Antonio, TX (US); Cristina Fuss, San Antonio, TX (US); Denes Marton, San Antonio, TX (US); Roger W. Wiseman, Bulverde, TX (US); Christopher E. Banas, San Antonio, TX (US); Christopher T. Boyle, San Antonio, TX (US); Steven R. Bailey, San Antonio, TX (US)

(73) Assignee: Advanced Bio Prosthetic Surfaces, Ltd., San Antonio, TX (US)

( * ) Notice: Subject to any disclaimer, the term of this patent is extended or adjusted under 35 U.S.C. 154(b) by 0 days.

(21) Appl. No.: 10/120,728

(22) Filed: Apr. 11, 2002

(65) Prior Publication Data
US 2003/0023303 A1 Jan. 30, 2003

Related U.S. Application Data

(63) Continuation-in-part of application No. 09/853,985, filed on May 11, 2001, now Pat. No. 6,849,085, and a continuation-in-part of application No. 09/477,120, filed on Dec. 31, 2000, now Pat. No. 6,458,153, and a continuation-in-part of application No. 09/443,929, filed on Nov. 19, 1999, now Pat. No. 6,379,383.

(60) Provisional application No. 60/302,797, filed on Jul. 3, 2001, provisional application No. 60/203,835, filed on May 12, 2000.

(51) Int. Cl.
*A61F 2/24* (2006.01)
*A61F 2/06* (2006.01)

(52) U.S. Cl. ................................ 623/2.18; 623/1.26
(58) Field of Classification Search ............... 623/2.18, 623/2.12, 1.26, 1.24
See application file for complete search history.

(56) References Cited

U.S. PATENT DOCUMENTS

| | | | |
|---|---|---|---|
| 3,717,883 A | 2/1973 | Mosher | 3/1 |
| 3,898,701 A | 8/1975 | LaRussa | 3/1.5 |
| 4,222,126 A | 9/1980 | Boretos et al. | 3/1.5 |
| 4,510,182 A | 4/1985 | Cornils et al. | 427/162 |
| 4,751,099 A | 6/1988 | Niino et al. | 427/34 |
| 4,846,834 A | 7/1989 | von Recum et al. | 623/11 |
| 4,994,077 A | 2/1991 | Dobben | 623/2 |

(Continued)

FOREIGN PATENT DOCUMENTS

DE  1452370  3/1974

(Continued)

OTHER PUBLICATIONS

"Liquid Sources for Chemical Vapor Deposition of Group 6 Metals and Metal Nitrides" by Gordon, et al., www.techtransfer.harvard.edu/cgi-bin/TALSearch.cgi?full_report=1&case=3, Case No. 1709.

(Continued)

*Primary Examiner*—Alvin J. Stewart
(74) *Attorney, Agent, or Firm*—David G. Rosenbaum; Paul J. Lee; Rosenbaum & Associates, PC

(57) ABSTRACT

This invention relates to improvements in prosthetic cardiac and venous valves and implantable medical devices having moveable septa. The inventive prosthetic cardiac and venous valves have metallic or pseudometallic valves coupled to metallic or pseudometallic stents that permit percutaneous delivery of the devices.

11 Claims, 6 Drawing Sheets

U.S. PATENT DOCUMENTS

| | | | |
|---|---|---|---|
| 5,049,251 A | 9/1991 | Inone | 204/192 |
| 5,061,914 A | 10/1991 | Busch et al. | 337/140 |
| 5,084,151 A | 1/1992 | Vallana | 204/192.11 |
| 5,108,420 A | 4/1992 | Marks | 606/213 |
| 5,133,845 A | 7/1992 | Vallana et al. | 204/192 |
| 5,158,750 A | 10/1992 | Finicle | 422/102 |
| 5,163,953 A | 11/1992 | Vince | 623/2 |
| 5,242,710 A | 9/1993 | Claar et al. | 427/248 |
| 5,277,933 A | 1/1994 | Claar et al. | 427/248 |
| 5,329,514 A | 7/1994 | Eguchi et al. | 369/126 |
| 5,332,402 A | 7/1994 | Teitelbaum | 623/2 |
| 5,334,217 A | 8/1994 | Das | 606/213 |
| 5,370,684 A | 12/1994 | Vallana et al. | 623/1 |
| 5,370,685 A | 12/1994 | Stevens | 623/2 |
| 5,376,463 A | 12/1994 | Bak et al. | 428/547 |
| 5,387,247 A | 2/1995 | Vallana et al. | 623/2 |
| 5,397,351 A | 3/1995 | Pavcnik et al. | 623/11 |
| 5,421,955 A | 6/1995 | Lau et al. | 216/48 |
| 5,477,864 A | 12/1995 | Davidson | 128/771 |
| 5,514,154 A | 5/1996 | Lau et al. | 606/195 |
| 5,540,820 A | 7/1996 | Terakado et al. | 204/192.3 |
| 5,545,210 A | 8/1996 | Hess et al. | 623/1 |
| 5,545,214 A | 8/1996 | Stevens | 623/2 |
| 5,569,295 A | 10/1996 | Lam | 606/198 |
| 5,593,442 A | 1/1997 | Klein | 623/12 |
| 5,603,721 A | 2/1997 | Lau et al. | 606/195 |
| 5,605,714 A | 2/1997 | Dearnaley et al. | 427/2.24 |
| 5,607,445 A | 3/1997 | Summers | 606/198 |
| 5,607,463 A | 3/1997 | Schwartz et al. | 623/1 |
| 5,609,629 A | 3/1997 | Fearnot et al. | 623/1 |
| 5,628,788 A | 5/1997 | Pinchuk | 623/1 |
| 5,630,840 A | 5/1997 | Mayer | 623/1 |
| 5,647,858 A | 7/1997 | Davidson | 604/264 |
| 5,649,951 A | 7/1997 | Davidson | 606/198 |
| 5,656,036 A | 8/1997 | Palmaz | 623/12 |
| 5,683,453 A | 11/1997 | Palmaz | 623/1 |
| 5,685,961 A | 11/1997 | Pourrezaei et al. | 204/192 |
| 5,690,670 A | 11/1997 | Davidson | 606/198 |
| 5,713,953 A | 2/1998 | Vallana et al. | 623/2 |
| 5,723,219 A | 3/1998 | Kolluri | 428/411.1 |
| 5,725,552 A | 3/1998 | Kotula et al. | 606/213 |
| 5,725,573 A | 3/1998 | Dearnaley et al. | 623/2 |
| 5,728,158 A | 3/1998 | Lau et al. | 623/12 |
| 5,735,896 A | 4/1998 | Amon et al. | 623/11 |
| 5,741,297 A | 4/1998 | Simon | 606/213 |
| 5,744,515 A | 4/1998 | Clapper | 523/113 |
| 5,765,418 A | 6/1998 | Rosenberg | 72/47 |
| 5,772,864 A | 6/1998 | Moller et al. | 205/73 |
| 5,776,161 A | 7/1998 | Globerman | 606/194 |
| 5,780,807 A | 7/1998 | Saunders | 219/121 |
| 5,782,908 A | 7/1998 | Cahalan et al. | 623/1 |
| 5,782,910 A | 7/1998 | Davidson | 623/3 |
| 5,788,558 A | 8/1998 | Klein | 451/136 |
| 5,798,042 A | 8/1998 | Chu et al. | 210/490 |
| 5,811,151 A | 9/1998 | Hendricks et al. | 427/2.24 |
| 5,824,045 A | 10/1998 | Alt | 623/1 |
| 5,824,049 A | 10/1998 | Ragheb | 623/1 |
| 5,824,056 A | 10/1998 | Rosenberg | 623/1 |
| 5,824,063 A | 10/1998 | Cox | 623/2 |
| 5,824,064 A | 10/1998 | Taheri | 623/2 |
| 5,840,009 A | 11/1998 | Fischell et al. | 600/3 |
| 5,840,081 A | 11/1998 | Andersen et al. | 623/2 |
| 5,843,117 A | 12/1998 | Alt et al. | 606/194 |
| 5,843,289 A | 12/1998 | Lee et al. | 204/192 |
| 5,846,261 A | 12/1998 | Kotula | 606/213 |
| 5,849,206 A | 12/1998 | Amon et al. | 216/63 |
| 5,855,597 A | 1/1999 | Jayaraman | 623/1 |
| 5,855,600 A | 1/1999 | Alt | 623/1 |
| 5,855,601 A | 1/1999 | Bessler et al. | 623/1 |
| 5,855,802 A | 1/1999 | Acciai et al. | 216/8 |
| 5,855,955 A | 1/1999 | Claar et al. | 427/248.1 |
| 5,858,556 A | 1/1999 | Eckert et al. | 428/586 |
| 5,866,113 A | 2/1999 | Hendricks et al. | 424/78.17 |
| 5,868,782 A | 2/1999 | Frantzen | 606/198 |
| 5,873,904 A | 2/1999 | Ragheb et al. | 623/1 |
| 5,876,432 A | 3/1999 | Lau et al. | 623/1 |
| 5,879,370 A | 3/1999 | Fischell et al. | 606/198 |
| 5,891,507 A | 4/1999 | Jayaraman | 427/2.25 |
| 5,895,406 A | 4/1999 | Gray et al. | 606/198 |
| 5,895,419 A | 4/1999 | Tweden et al. | 623/2 |
| 5,899,935 A | 5/1999 | Ding | 623/1 |
| 5,907,893 A | 6/1999 | Zadno-Azizi | 29/6.1 |
| 5,913,896 A | 6/1999 | Boyle et al. | 623/1 |
| 5,919,224 A | 7/1999 | Thompson et al. | 623/1 |
| 5,919,225 A | 7/1999 | Lau et al. | 623/1 |
| 5,925,063 A * | 7/1999 | Khosravi | 606/200 |
| 5,932,299 A | 8/1999 | Katoot | 427/508 |
| 5,938,682 A | 8/1999 | Hojeibane et al. | 606/198 |
| 5,938,697 A | 8/1999 | Killion et al. | 623/1 |
| 5,945,153 A | 8/1999 | Dearnaley | 427/2.12 |
| 5,951,881 A | 9/1999 | Rogers et al. | 216/41 |
| 5,954,766 A | 9/1999 | Zadno-Azizi et al. | 623/2 |
| 5,955,588 A | 9/1999 | Tsang et al. | 536/21 |
| 5,957,573 A | 9/1999 | Wedekind et al. | 623/1 |
| 5,957,949 A | 9/1999 | Leonhardt et al. | 606/194 |
| 5,962,138 A | 10/1999 | Kolluri et al. | 428/411.1 |
| 5,964,782 A | 10/1999 | Lafontaine et al. | 606/213 |
| 5,968,091 A | 10/1999 | Pinchuk et al. | 623/1 |
| 5,972,018 A | 10/1999 | Israel et al. | 606/198 |
| 5,972,027 A | 10/1999 | Johnson | 623/1 |
| 5,984,905 A | 11/1999 | Dearnaley et al. | 604/265 |
| 6,013,855 A | 1/2000 | McPherson | 623/11 |
| 6,015,429 A | 1/2000 | Lau et al. | 623/1 |
| 6,019,784 A | 2/2000 | Hines | 623/1 |
| 6,022,370 A | 2/2000 | Tower | 606/194 |
| 6,027,526 A | 2/2000 | Limon et al. | 623/1 |
| 6,033,433 A | 3/2000 | Ehr et al. | 623/1 |
| 6,042,597 A | 3/2000 | Kveen et al. | 606/198 |
| 6,056,776 A | 5/2000 | Lau et al. | 623/1 |
| 6,059,808 A | 5/2000 | Boussignac et al. | 606/191 |
| 6,066,167 A | 5/2000 | Lau et al. | 623/1 |
| 6,066,168 A | 5/2000 | Lau et al. | 623/1 |
| 6,066,169 A | 5/2000 | McGuiness | 623/1.16 |
| 6,071,305 A | 6/2000 | Brown et al. | 623/1 |
| 6,086,773 A | 7/2000 | Dufresne et al. | 216/8 |
| 6,096,175 A | 8/2000 | Roth | 204/192 |
| 6,106,642 A | 8/2000 | DiCarlo et al. | 148/563 |
| 6,299,637 B1 * | 10/2001 | Shaolian et al. | 623/1.24 |
| 6,312,463 B1 | 11/2001 | Rourke et al. | 623/1.39 |
| 6,425,916 B1 | 7/2002 | Garrison et al. | 623/2.11 |
| 6,544,291 B2 * | 4/2003 | Taylor | 623/23.68 |
| 2001/0039449 A1 | 11/2001 | Johnson et al. | 623/1.19 |

FOREIGN PATENT DOCUMENTS

| | | |
|---|---|---|
| EP | 0331345 A2 * | 2/1989 |
| EP | 0 400 947 | 5/1990 |
| EP | 0 442 303 | 1/1991 |
| EP | 0 850 607 | 7/1998 |
| EP | 0 808 614 | 11/1998 |
| JP | 51055724 | 5/1976 |
| JP | 61-88135 | 7/1994 |
| JP | 11267462 | 10/1999 |
| WO | WO97/07257 | 2/1997 |
| WO | 97/44692 | 11/1997 |
| WO | 98/13537 | 4/1998 |
| WO | 98/45506 | 10/1998 |
| WO | 99/23977 | 5/1999 |
| WO | WO99/62432 | 12/1999 |
| WO | 01/19285 | 3/2001 |
| WO | WO01/53559 | 7/2001 |
| WO | WO01/55473 | 8/2001 |

| WO | WO01/56502 | 8/2001 |
| WO | WO2002/024119 A1 * | 3/2002 |

OTHER PUBLICATIONS

"Fabrication of Small-Scale Coils and Bands as Photomasks on Optical Fibers for Generation of In-Fiber Gratings, Electromagnets as Micro-NMR Coils, Microtransformers, and Intra-Vascular Stents" www.techtransfer.harvard.edu/cgi-bin/TALSearch. cgi?full_report=1&case=72, Case No. 1263.

"Reactions of Biological Cells to Nanostructures", by Curtis, et al., AVS 46th International Symposium, Paper BI-WeM2 (Oct. 27, 1999).

"Biocompatibility of Cardiac Cells on Silane-Modified Surfaces" AVS 46th International Symposium, Paper BI-WeM5 (Oct. 27, 1999).

"Biofunctionalization of Surfaces with Peptide Amphilphiles" AVS 46th International Symposium, Paper No. BI-WeM7 (Oct. 27, 1999).

"Plasma Copolymer Surfaces for Cell Culture" AVS 46th International Symposium, Paper No. Paper BI-WeM9 (Oct. 27, 1999).

"Plasma Co-polymer Surfaces for the Controlled Adsorption of Common Proteins" AVS 46th International Symposium, Paper No. BI-FrM2 (Oct. 29, 1999).

"Biofilm—Titanium Chemistry of Adhesion Using X-ray Photoelectron Spectroscopy" AVS 46th International Symposium, Paper No. BI-FrM10.

"Nanoscale Patterning of Gold for Attachment of Supported Lipid Bilayers" AVS 46th International Symposium, Paper No. BI-FrM10.

"Focused Ion Beam NonaFabrication", http://www.glue.umd.edu/~astan/avs04.htm.

"Amorphous Carbon and C:N Thin Films" http://www.glue.umd.edu/~astan/avs01.htm.

Multilayer Ceramic/Metallic Coatings by Ion Beam-Assisted, Electron Beam Physical Vapor (EB-PVD) Deposition, Penn State Appled Research Laboratory, pp. 1-4 (1997).

"Benefits From Diamond-Like Coated Stainless Steel Stents", http://www.phytis.com/stents0.htm, pp. 1-2.

"Adhesion of Bovine Serus Albumin on Coated DLC (Diamond-Like) and Uncoated ($SiO_2$/$TiO_2$) Sensor Chips", http://www.phytis.com/stent4.htm, pp. 1-2.

"Flow Cytometric Investigation", http://www.phytis.com/stent6.htm, pp. 1-3.

"Pre-clinical and Clinical Evaluation", http://www.phytis.com/stent2.htm, pp. 1-2.

"The New Phytis Stent", http://www.phytis.com/stent1.htm, pp. 1-2.

"Invulnerability and Resistance of DLC-Coating", http://www.phytis.com/stent3.htm, pp. 1-3.

"Material In Use and Its Biocompatibility", http://www.phytis.com/stent5.htm, pp. 1-2.

"Expertise Concerning the Implementation of the Phytis Diamond as Stent Performed at the Institute for Experimental Medicine (IEM)", http://www.phytis.com/stent9.htm, pp. 1.

"Phytis L.D.A. Home Page information", http://www.phytis.com/content/htm, pp. 1-15.

"Risk Analysis of Stents With a Diamond-Like Coated Surface For Use in Prosthetic Implants", http://www.phytis.com/risk.htm, pp. 1-6.

"Directions for Use, DIAMOND AS® Stent", http://www.phytis.com/direcuse.htm, pp. 1-8.

"Stents: Literature", http://www.phytis.com/liter.htm, pp. 1-8.

"Vacuum Conditions for Sputtering Thin Film TiNi", *Journal of Vacuum Science and Technology, JVST A Online*, pp. 1-2 (Abstract view).

"Oriented nickel-tetanium shape memory alloy films prepared by annealing during deposition", by Kathleen Gisser, et al., *Applied Physics Letters*, vol. 61, Issue 14, pp. 1632-1634 (Abstract view).

"Relative importance of bombardment energy and intensity in ion plating", K.S. Fancey, et al., *Journal of Vacuum Science & Technology A: Vacuum, Surfaces and Films*, vol. 13, Issue 2, pp. 428-435 (Abstract view) Mar. 1995.

"MASA Heart Valves", http://www.heart-surgeons.com/valvedesign.htm, pp. 1-3.

"Aortic Valve Replacement", *STS Patient Information*, http://www.sts.org/doc/3620, pp. 1-5.

"Minimally Invasive Aortic Valve Surgery" *CTSNET Experts' Techniques*, http://www.ctsnet.org/doc.3358, pp. 1-4.

"Heart Annouces Launch of Heartport InSite AVR System for Less Invasive Aortic Valve Replacement" *Heartport, Inc. Company Press Release*, pp. 1-2.

"ATS Medical Inc. Annual Report", pp. 1-7.

"St. Jude Medical Heart Valve Division Expanding the Focus", www.sum.com/stjde/world.htm/expand.htm.

"Applications of Shape-Memory Alloy Thin Films" by A.D. Johnson and V.V. Martynov, *Proceedings of the Second International Conference on Shape Memory and Superelastic Technologies Asilomar Conference Center, Pacific Grove, California, USA*, pp. 1-8 (1997).

"Sputter-deposition of TiNi, TiNiPd films displaying the two-way shape-memory effect" by E. Quandt, et al., *Sensors and Actuators*, A 53, pp. 434-439 (1996).

"Thin-film Processing of TiNi Shape Memory Alloy" by J.A. Waker and K.J. Gabriel, *Sensors and Actuators*, A21-A23, pp. 243-246 (1990).

"The Effects of Ion Irradiation on NiTi Shape Memory Alloy Thin Films" by F. Goldberg and E. Knystautas, *Proceedings of the Second International Conference on Shape Memory and Superelastic Technologies Asilomar Conference Center, Pacific Grove, California, USA*, pp. 177-182 (1997).

"Constitutive Parts of a Shape Memory Alloy Titanium Nickel Thin Film Catheter" by L. Buchaillot, et al., *Proceedings of the Second International Conference on Shape Memory and Superelastic Technologies Asilomar Conference Center, Pacific Grove, California, USA*, pp. 183-188 (1997).

"The Effect of HCD Technological Factors on the NiTi SMA Film Thickness" by Q. Pingshan, et al., *Proceedings of the Second International Conference on Shape Memory and Superelastic Technologies Asilomar Conference Center, Pacific Grove, California, USA*, pp. 173-176 (1997).

"The Characteristics of NiTi HCD-Deposited SMA Films" by H. Weixin, et al., *Proceedings of the Second International Conference on Shape Memory and Superelastic Technologies Asilomar Conference Center, Pacific Grove, California, USA*, pp. 167-172 (1997).

"Microstructure of Ti-Rich TiNi Thin Films" by A. Ishida, et al., *Proceedings of the Second International Conference on Shape Memory and Superelastic Technologies Asilomar Conference Center, Pacific Grove, California, USA*, pp. 161-166 (1997).

"Thin Film Shape Memory Alloy Microactuators" by TiNi Alloy Company (online).

"Progress in Thin Film Shape Memory Microactuators" by Johnson, et al., www.sma-mems.com/recent.htm (Overview), pp. 1-5.

"The influence of ion irradiation during film growth on the chemical stability of film/substrate systems" by W. Ensinger, *Surface and Coatings Technology*, vol. 80, pp. 35-48 (1996).

"Sputtering Targets High-Quality Thin Film Materials" by AMETEK Specialty Metal Products online at www.ametek84.com/fd-sputtering.html, pp. 1-3.

"A Concise History of Vacuum Coating Technology, Part 2: 1940 to 1975" by D. Mattox, www.svc.org/HistoryofVac2.html, pp. 1-15.

"Model Surfaces for Studying and Controlling the Adhesion of Cells" by M. Mrksich, AVS 47th International Symposium, Invited Paper No. BI+EL-TuA1 (Oct. 3, 2000).

"Cell Response to Chemically and Topographically Modified Surfaces" by D.S. Sutherland, et al., AVS 47th International Symposium, Paper No. BI+EL-TuA3 (Oct. 3, 2000).

"Tissue Formation of Hepatocytes on Micro-Porous Films of Polylactide" by T. Nishikawa, et al., AVS 47th International Symposium, Paper No. BI+EL-TuA10 (Oct. 3, 2000).

"Endothelial Cell Organization on Micropatterned Protein Surfaces" by R. Daw, et al., AVS 47th International Symposium, Paper No. BI-WeP21 (Oct. 4, 2000).

"The Nanomechanical Properties of Thin Films" by J.E. Houston, AVS 47th International Symposium, Paper No. TF-TuA1 (Oct. 3, 2000).

"Anomalous Plastic and Elastic Behaviors of Sputter-deposited TiN with 10 or 20 Inserted Thin Al Layers Evaluated by Nanoindentation" by E. Kusano, et al., AVS 47th International Symposium, Paper No. TF-TuA3 (Oct. 3, 2000).

"Recent Progress in the Application of Thin Film Shape Memory Alloys" by A.D. Johnson and J.D. Busch, *Proceedings of the First International Conference on Shape Memory and Superelastic Technologies Asilomar Conference Center, Pacific Grove, California, USA*, pp. 299-310 (1994).

"Shape Memory Properties in NiTI Sputter-deposited Film", by J.D. Busch and A.D. Johnson, *J Appl. Phys*, vol. 68, No. 12, pp. 6224-6226 (Dec. 15, 1990).

"Multicomponent Film Deposition by Target Biasing" by *IBM Technical Disclosure Bulletin*, pp. 1-2 (Jul. 1980.

* cited by examiner

VALVULAR PROSTHESES HAVING METAL OR PSEUDOMETALLIC CONSTRUCTION AND METHODS OF MANUFACTURE

CROSS-REFERENCE TO RELATED INVENTIONS

This application corresponds to and claims priority from U.S. Provisional Application Ser. No. 60/302,797 filed Jul. 3, 2001 and is a continuation-in-part of U.S. patent application Ser. No. 09/443,929, filed Nov. 19, 1999 now U.S. Pat. No. 6,379,383, U.S. patent application Ser. No. 09/477,120, filed Dec. 31, 2000, now U.S. Pat. No. 6,458,153 and U.S. patent application Ser. No. 09/853,985 filed May 11, 2001 now U.S. Pat. No. 6,849,085, which claims priority from U.S. Provisional Patent Application No. 60/203,835, filed May 12, 2000.

BACKGROUND OF THE INVENTION

The present invention relates generally to metal and pseudometallic films suitable for implantation into mammalian subjects in need thereof. More particularly, the present invention pertains to prosthetic cardiac and venous valve implants, access ports and other implantable medical devices that employ moveable valve flaps. The implantable medical devices according to the present invention have improved valve flap members fabricated from metal and/or pseudometallic materials. It is desirable, although not essential to the present invention, that the prosthetic cardiac and venous valve implants be capable of being delivered using endovascular techniques and being implanted at an intracardiac or intravenous site without the need for anatomic valve removal. Embodiments of the prosthetic valves of the present invention are well-suited for cardiac delivery via a femoral or subclavian artery approach using a delivery catheter, and, depending upon the specific configuration selected, may be deployed within the heart to repair valve defects or disease or septal defects or disease. According to one embodiment of the invention, there is provided a chamber-to-vessel (CV) configuration that is particularly well suited as an aortic valve prosthesis to facilitate blood flow from the left ventricle to the aorta. In a second embodiment, there is provided a prosthetic valve in a chamber-to-chamber (CC) configuration that is particularly well-adapted for mitral valve replacement or repair of septal defects. Finally, a third embodiment is provided in a vessel-to-vessel (VV) configuration, which is well suited for venous valve exclusion and replacement.

Common to each of the CV, CC and VV embodiments of the present invention are a stent support member, a graft member which covers at least a portion of either or both the luminal and abluminal surfaces of the stent and valve flap members. Both the graft member and the valve flap members are preferably fabricated from metallic and/or pseudometallic materials, the valve flaps being coupled to the stent in a manner which biases the valve flaps so they close upon a zero pressure differential across the valve region.

More specifically, the valve flap members and the graft members of the present invention are fabricated entirely of self-supporting films made of biocompatible metals or biocompatible pseudometals. For purposes of this application, the term "pseudometal" or "pseudometallic" is intended to mean a biocompatible material which exhibits biological response and material characteristics substantially the same as biocompatible metals, such as for example composite materials.

As opposed to wrought materials that are made of a single metal or alloy, the inventive valve flap members and graft members are made of at least two layers formed upon one another into a self-supporting laminate structure. Laminate structures are generally known to increase the mechanical strength of sheet materials, such as wood or paper products. Laminates are used in the field of thin film fabrication also to increase the mechanical properties of the thin film, specifically hardness and toughness. Laminate metal foils have not been used or developed because the standard metal forming technologies, such as rolling and extrusion, for example, do not readily lend themselves to producing laminate structures. Vacuum deposition technologies can be developed to yield laminate metal structures with improved mechanical properties. In addition, laminate structures can be designed to provide special qualities by including layers that have special properties such as superelasticity, shape memory, radio-opacity, corrosion resistance etc.

It is important for the present invention to provide orientational definitions. For purposes of the present invention, references to positional aspects of the present invention will be defined relative to the directional flow vector of blood flow through the implantable device. Thus, the term "proximal" is intended to mean on the inflow or upstream flow side of the device, while "distal" is intended to mean on the outflow or downstream flow side of the device. With respect to the catheter delivery system described herein, the term "proximal" is intended to mean toward the operator end of the catheter, while the term "distal" is intended to mean toward the terminal end or device-carrying end of the catheter.

Conventional metal foils, wires and thin-walled seamless tubes are typically produced from ingots in a series of hot or cold forming steps that include some combination of rolling, pulling, extrusion and other similar processes. Each of these processing steps is accompanied by auxiliary steps that include cleaning the surfaces of the material of foreign material residues deposited on the material by the tooling and lubricants used in the metal forming processes. Additionally, chemical interaction with tooling and lubricant materials and ambient gases also introduces contaminants. Some residue will still usually remain on the surface of the formed material, and there is a high probability that these contaminating residues become incorporated during subsequent processing steps into the bulk of the wrought metal product. With decreasing material product size, the significance of such contaminating impurities increases. Specifically, a greater number of process steps, and, therefore, a greater probability for introducing contaminants, are required to produce smaller product sizes. Moreover, with decreasing product size, the relative size of non-metal or other foreign inclusions becomes larger. This effect is particularly important for material thicknesses that are comparable to the grain or inclusion size. For example, austenitic stainless steels have typical grain sizes on the order of magnitude of 10–100 micrometer. When a wire or foil with a thickness in this range is produced, there is significant probability that some grain boundaries or defects will extend across a large portion or even across the total thickness of the product. Such products will have locally diminished mechanical and corrosion resistance properties. While corrosion resistance is remedied by surface treatments such as electropolishing, the mechanical properties are more difficult to control.

The mechanical properties of metals depend significantly on their microstructure. The forming and shaping processes used to fabricate metal foils, wires and thin-walled seamless tubes involves heavy deformation of a bulk material, which results in a heavily strained and deformed grain structure. Even though annealing treatments may partially alleviate the grain deformation, it is typically impossible to revert to well-rounded grain structure and a large range of grain sizes is a common result. The end result of conventional forming and shaping processes, coupled with annealing, typically results in non-uniform grain structure and less favorable mechanical properties in smaller sized wrought metal products. It is possible, therefore, to produce high quality homogeneous materials for special purposes, such as micromechanical devices and medical devices, using vacuum deposition technologies.

In vacuum deposition technologies, materials are formed directly in the desired geometry, e.g., planar, tubular, etc. The common principle of the vacuum deposition processes is to take a material in a minimally processed form, such as pellets or thick foils (the source material) and atomize them. Atomization may be carried out using heat, as is the case in physical vapor deposition, or using the effect of collisional processes, as in the case of sputter deposition, for example. In some forms of deposition, a process, such as laser ablation, which creates microparticles that typically consist of one or more atoms, may replace atomization; the number of atoms per particle may be in the thousands or more. The atoms or particles of the source material are then deposited on a substrate or mandrel to directly form the desired object. In other deposition methodologies, chemical reactions between ambient gas introduced into the vacuum chamber, i.e., the gas source, and the deposited atoms and/or particles are part of the deposition process. The deposited material includes compound species that are formed due to the reaction of the solid source and the gas source, such as in the case of chemical vapor deposition. In most cases, the deposited material is then either partially or completely removed from the substrate, to form the desired product.

The rate of film growth is a significant parameter of vacuum deposition processes. In order to deposit materials that can be compared in functionality with wrought metal products, deposition rates in excess of 1 micrometers/hour are a must and indeed rates as high as 100 micrometers per hour are desirable. These are high deposition rates and it is known that at such rates the deposits always have a columnar structure. Depending on other deposition parameters, and most importantly on the substrate temperature, the columns may be amorphous or crystalline but at such high deposition rates microcrystalline structure development can be expected at best. The difficulty is that the columns provide a mechanically weak structure in which crack propagation can occur uninhibited across the whole thickness of the deposit.

A special advantage of vacuum deposition technologies is that it is possible to deposit layered materials and thus films possessing exceptional qualities may be produced (cf., H. Holleck, V. Schier: "Multilayer PVD coatings for wear protection", *Surface and Coatings Technology*, Vol. 76–77 (1995) pp. 328–336). Layered materials, such as superstructures or multilayers, are commonly deposited to take advantage of some chemical, electronic, or optical property of the material as a coating; a common example is an antireflective coating on an optical lens.

It has not been recognized until relatively recently that multilayer coatings may have improved mechanical properties compared with similar coatings made of a single layer. The improved mechanical properties may be due to the ability of the interface between the layers to relieve stress. This stress relief occurs if the interface provides a slide plane, is plastic, or may delaminate locally. This property of multilayer films has been recognized in regard with their hardness but this recognition has not been translated to other mechanical properties that are significant for metal products that may be used in application where they replace wrought metal parts.

A technological step that interrupts the film growth results in discontinuous columns and prevents crack propagation across the entire film thickness. In this sense, it is not necessary that the structure consist of a multiplicity of chemically distinct layers, as it is common in the case of thin film technology where multilayers are used. Such chemical differences may be useful and may contribute to improved properties of the materials.

As used in this application a "layer" is intended to mean a substantially uniform material limited by interfaces between it and adjacent other substantially homogeneous layers, substrate, or environment. The interface region between adjacent layers is an inhomogeneous region in which extensive thermodynamic parameters may change. Different layers are not necessarily characterized by different values of the extensive thermodynamic parameters but at the interface, there is a local change at least in some parameters. For example, the interface between two steel layers that are identical in composition and microstructure may be characterized by a high local concentration of grain boundaries due to an interruption of the film growth process. Thus, the interface between layers is not necessarily different in chemical composition if it is different in structure.

It is necessary to provide for good adhesion between the layers and this is usually achieved by providing for a relatively broad interface region rather than for an abrupt interface. The width of the interface region may be defined as the range within which extensive thermodynamic parameters change. This range can depend on the interface area considered and it may mean the extent of interface microroughness. In other words, adhesion may be promoted by increased interface microroughness between adjacent layers.

By providing for a layered structure, the inventive materials consist of a controlled maximum size of grains and columns as extended defects in the direction of the film growth (perpendicular to the layers). This limit of the grain or defect size results in materials that have increased mechanical strength and particularly increased toughness compared to their non-laminated counterparts, both deposited and wrought materials. In addition, limiting the extent to which defects and grain boundaries reach across the laminate, corrosion resistance is also improved.

Laminated materials will have additional advantages when chemical compositions of the layers are chosen to achieve special properties. For example, a radiopaque material such as tantalum may form one layer of a structure while other layers are chosen to provide the material with necessary mechanical and other properties.

Heretofore, however, conventional implantable valves have traditionally been fabricated of rigid metal or synthetic materials, or have been fabricated of pliant synthetic polymeric materials, each of which involved both hemodynamic and physiological complications.

SUMMARY OF PRIOR ART

The prior art discloses certain common device segments inherently required by a percutaneous prosthetic valve: an expandable stent segment, an anchoring segment and a flow-regulation segment.

Prior art percutaneous prosthetic valve devices include the Dobben valve, U.S. Pat. No. 4,994,077, the Vince valve, U.S. Pat. No. 5,163,953, the Teitelbaum valve, U.S. Pat. No. 5,332,402, the Stevens valve, U.S. Pat. No. 5,370,685, the Pavcnik valve, U.S. Pat. No. 5,397,351, the Taheri valve, U.S. Pat. No. 5,824,064, the Anderson valves, U.S. Pat. Nos. 5,411,552 & 5,840,081, the Jayaraman valve, U.S. Pat. No. 5,855,597, the Besseler valve, U.S. Pat. No. 5,855,601, the Khosravi valve, U.S. Pat. No. 5,925,063, the Zadano-Azizi valve, U.S. Pat. No. 5,954,766, and the Leonhardt valve, U.S. Pat. No. 5,957,949. Each of these pre-existing stent valve designs has certain disadvantages which are resolved by the present invention.

The Dobben valve has a disk shaped flap threaded on a wire bent like a safety pin to engage the vessel wall and anchor the valve. A second embodiment uses a stent of a cylindrical or crown shape that is made by bending wire into a zig-zag shape to anchor the device and attach the flow regulator flap. The device presents significant hemodynamic, delivery, fatigue and stability disadvantages.

The Vince valve has a stent comprised of a toroidal body formed of a flexible coil of wire and a flow-regulation mechanism consisting of a flap of biologic material. Numerous longitudinal extensions within the stent are provided as attachment posts to mount the flow-regulation mechanism. The device requires balloon expansion to deliver to the body orifice. The main shortcoming of this design is delivery profile. Specifically, the device and method put forth will require a 20+ French size catheter (approximately 9 French sizes to accommodate the balloon and 14+ French sizes to accommodate the compressed device) making the device clinically ineffective as a minimally invasive technique. Additionally, the device does not adequately address hemodynamic, stability and anchoring concerns.

The Teitelbaum valve is made of shape memory nitinol and consists of two components. The first component is stent-like and comprised of a meshwork or braiding of nitinol wire similar to that described by Wallsten, U.S. Pat. No. 4,655,771, with trumpet like distal a proximal flares. The purpose of the stent is to maintain a semi-ridged patent channel through the diseased cardiac valve after initial balloon dilation. The flared ends are intended to maintain the position of the stent component across the valve thereby anchoring the device. Embodiments for the flow-regulation mechanism include a sliding obturator and a caged ball both which are delivered secondary to the stent portion. The disadvantages of the device are the flow regulators reduce the effective valve orifice and generate sub-optimal hemodynamic characteristics; fatigue concerns arise from the separate nature of the stent and flow-regulation components; the high metal and exposed metal content raises thrombogenesis, valvular stenosis and chronic anticoagulation concerns; and the separate delivery requirements (although addressing the need for small delivery profile) in addition to any initial valvuloplasty performed increases the time, costs, risks, difficulty and trauma associated with the percutaneous procedure.

The Pavcnik valve is a self-expanding percutaneous device comprised of a poppet, a stent and a restraining element. The valve stent has barbed means to anchor to the internal passageway. The device includes a self-expanding stent of a zigzag configuration in conjunction with a cage mechanism comprised of a multiplicity of crisscrossed wires and a valve seat. The disadvantages of the device include large delivery profile, reduced effective valvular orifice, possible perivalvular leakage, trauma-inducing turbulent flow generated by the cage occlusive apparatus and valve seat, thrombogenesis, valvular stenosis, chronic anticoagulation, problematic physiological and procedural concerns due to the barb anchors and complex delivery procedure that includes inflation of occlusive member after initial implantation.

Stevens discloses a percutaneous valve replacement system for the endovascular removal of a malfunctioning valve followed by replacement with a prosthetic valve. The valve replacement system may include a prosthetic valve device comprised of a stent and cusps for flow-regulation such as a fixed porcine aortic valve, a valve introducer, an intraluminal procedure device, a procedure device capsule and a tissue cutter. The devices disclosed indicate a long and complex procedure requiring large diameter catheters. The valve device disclosed will require a large delivery catheter and does not address the key mechanisms required of a functioning valve. Additionally, the device requires intraluminal-securing means such as suturing to anchor the device at the desired location.

The Taheri valve describes an aortic valve replacement combined with an aortic arch graft. The devices and percutaneous methods described require puncture of the chest cavity.

Anderson has disclosed various balloon expandable percutaneous prosthetic valves. The latest discloses a valve prosthesis comprised of a stent made from an expandable cylindrical structure made of several spaced apices and an elastically collapsible valve mounted to the stent with the commissural points of the valve mounted to the apices. The device is placed at the desired location by balloon expanding the stent and valve. The main disadvantage to this design is the 20+ French size delivery requirement. Other problems include anchoring stability, perivalvular leakage, difficult manufacture and suspect valve performance.

The Jayaraman valve includes a star-shaped stent and a replacement valve and/or replacement graft for use in repairing a damaged cardiac valve. The device is comprised of a chain of interconnected star-shaped stent segments in the center of which sits a replacement valve. The flow-regulation mechanism consists of three flaps cut into a flat piece of graft material that is rolled to form a conduit in which the three flaps may be folded inwardly in an overlapping manner. An additional flow-regulation mechanism is disclosed in which a patch (or multiple patches) is sutured to the outside of a conduit which is then pulled inside out or inverted such that the patch(s) reside on the fully inverted conduit. A balloon catheter is required to assist expansion during delivery. The disadvantages of this design include lack of sufficient anchoring mechanism; problematic interference concerns with adjacent tissues and anatomical structures; fatigue concerns associated with the multiplicity of segments, connections and sutures; lack of an adequately controlled and biased flow-regulation mechanism; uncertain effective valve orifice, difficult manufacture; balloon dilation requirement; complex, difficult and inaccurate delivery and large delivery profile.

The Besseler valve discloses methods and devices for the endovascular removal of a defective heart valve and the replacement with a percutaneous cardiac valve. The device is comprised of a self-expanding stent member with a flexible valve disposed within. The stent member is of a self-expanding cylindrical shape made from a closed wire in formed in a zigzag configuration that can be a single piece, stamped or extruded or formed by welding the free ends together. The flow-regulation mechanism is comprised of an arcuate portion which contains a slit (or slits) to form leaflets and a cuff portion which is sutured to and encloses the stent.

The preferred flow regulator is a porcine pericardium with three cusps. An additional flow regulator is described in which the graft material that comprises the leaflets (no additional mechanisms for flow-regulation) extends to form the outer cuff portion and is attached to the stent portion with sutures. The anchoring segment is provided by a plurality of barbs carried by the stent (and therefor penetrating the cuff-graft segment). Delivery requires endoluminal removal of the natural valve because the barb anchors will malfunction if they are orthotopically secured to the native leaflets instead of the more rigid tissue at the native annulus or vessel wall. Delivery involves a catheter within which the device and a pusher rod are disposed. The disadvantages of the device are lack of a well defined and biased flow-regulation mechanism, anatomic valve removal is required thereby lengthening the procedure time, increasing difficulty and reducing clinical practicality, trauma-inducing barbs as described above and the device is unstable and prone to migration if barbs are omitted.

The Khosravi valve discloses a percutaneous prosthetic valve comprised of a coiled sheet stent similar to that described by Derbyshire, U.S. Pat. No. 5,007,926, to which a plurality of flaps are mounted on the interior surface to form a flow-regulation mechanism that may be comprised of a biocompatible material. The disadvantages of this design include problematic interactions between the stent and flaps in the delivery state, lack of clinical data on coiled stent performance, the lack of a detailed mechanism to ensure that the flaps will create a competent one-directional valve, lack of appropriate anchoring means, and the design requirements imposed by surrounding anatomical structures are ignored.

The Zadno-Azizi valve discloses a device in which flow-regulation is provided by a flap disposed within a frame structure capable of taking an insertion state and an expanded state. The preferred embodiment of the flow-regulation mechanism is defined by a longitudinal valve body made of a sufficiently resilient material with a slit(s) that extends longitudinally through the valve body. Increased sub-valvular pressure is said to cause the valve body to expand thereby opening the slit and allowing fluid flow there through. The valve body extends into the into the lumen of the body passage such that increased supra-valvular pressure will prevent the slit from opening thereby effecting one-directional flow. The device includes embedding the frame within the seal or graft material through injection molding, blow molding and insertion molding. The disadvantages of the device include the flow-regulation mechanism provides a small effective valve orifice, the turbidity caused by the multiple slit mechanisms, the large delivery profile required by the disclosed embodiments and the lack of acute anchoring means.

Finally, the Leonhardt valve is comprised of a tubular graft having radially compressible annular spring portions and a flow regulator, which is preferably a biological valve disposed within. In addition to oversizing the spring stent by 30%, anchoring means is provided by a light-activated biocompatible tissue adhesive is located on the outside of the tubular graft and seals to the living tissue. The stent section is comprised of a single piece of superelastic wire formed into a zigzag shape and connected together by crimping tubes, adhesives or welds. A malleable thin-walled, biocompatible, flexible, expandable, woven fabric graft material is connected to the outside of the stent that is in turn connected to the biological flow regulator. Disadvantages of this device include those profile concerns associated with biological valves and unsupported graft-leaflet regulators, a large diameter complex delivery system and method which requires multiple anchoring balloons and the use of a light activated tissue adhesive in addition to any prior valvuloplasty performed, interference with surrounding anatomy and the questionable clinical utility and feasibility of the light actuated anchoring means.

As used herein the term "Graft" is intended to indicate any type of tubular member which exhibits integral columnar and circumferential strength and which has openings which pass through the thickness of the tubular member In accordance with a preferred embodiment of the invention, a graft member is formed as a discrete thin sheet or tube of biocompatible metal and/or pseudometal. A plurality of openings is provided which pass transversely through the graft member. The plurality of openings may be random or may be patterned. It is preferable that the size of each of the plurality of openings be such as to permit cellular migration through each opening, without permitting fluid flow there through. In this manner, blood cannot flow through the plurality of openings, but various cells or proteins may freely pass through the plurality of openings to promote graft healing in vivo. In accordance with another aspect of the inventive graft embodiment, it is contemplated that two graft members are employed, with an outer diameter of a first graft member being smaller than the inner diameter of a second graft member, such that the first graft member is concentrically engageable within a lumen of the second graft member. Both the first and second graft members have a pattern of a plurality of openings passing there through. The first and second graft members are positioned concentrically with respect to one another, with the plurality of patterned openings being positioned out of phase relative to one another such as to create a tortuous cellular migration pathway through the wall of the concentrically engaged first and second graft members. In order to facilitate cellular migration through and healing of the first and second graft members in vivo, it is preferable to provide additional cellular migration pathways that communicate between the plurality of openings in the first and second graft members. These additional cellular migration pathways may be imparted as 1) a plurality of projections formed on either the luminal surface of the second graft or the abluminal surface of the first graft, or both, which serve as spacers and act to maintain an annular opening between the first and second graft members that permits cellular migration and cellular communication between the plurality of openings in the first and second graft members, or 2) a plurality of microgrooves, which may be random, radial, helical, or longitudinal relative to the longitudinal axis of the first and second graft members, the plurality of microgrooves being of a sufficient size to permit cellular migration and propagation along the groove without permitting fluid flow there through, the microgrooves serve as cellular migration conduits between the plurality of openings in the first and second graft members.

In order to improve healing response, it is preferable that the materials employed have substantially homogenous surface profiles at the blood or tissue contact surfaces thereof. A substantially homogeneous surface profile is achieved by controlling heterogeneities along the blood or tissue-contacting surface of the material. The heterogeneities that are controlled in accordance with an embodiment of the present invention include: grain size, grain phase, grain material composition, stent-material composition, and surface topography at the blood flow surface of the stent. Additionally, the present invention provides methods of making endoluminal devices having controlled heterogeneities in the device material along the blood flow or tissue-contacting surface of the device. Material heterogeneities are preferably controlled by using conventional methods of vacuum deposition of materials onto a substrate.

The surface of a solid, homogeneous material can be conceptualized as having unsaturated inter-atomic and inter-molecular bonds forming a reactive plane ready to interact with the environment. In practice, a perfectly clean surface is unattainable because of immediate adsorption of airborne species, upon exposure to ambient air, of O, $O_2$, $CO_2$, $SO_2$, NO, hydrocarbons and other more complex reactive molecules. Reaction with oxygen implies the formation of oxides on a metal surface, a self-limiting process, known as passivation. An oxidized surface is also reactive with air, by adsorbing simple, organic airborne compounds. Assuming the existence of bulk material of homogeneous subsurface and surface composition, oxygen and hydrocarbons may adsorb homogeneously. Therefore, further exposure to another environment, such as the vascular compartment, may be followed by a uniform biological response.

Current metallic vascular devices, such as stents, are made from bulk metals made by conventional methods which employ many steps that introduce processing aides to the metals make stent precursors, such as hypotubes. For example, olefins trapped by cold drawing and transformed into carbides or elemental carbon deposit by heat treatment, typically yield large carbon rich areas in 316L stainless steel tubing manufactured by cold drawing process. The conventional stents have marked surface and subsurface heterogeneity resulting from manufacturing processes (friction material transfer from tooling, inclusion of lubricants, chemical segregation from heat treatments). This results in formation of surface and subsurface inclusions with chemical composition and, therefore, reactivity different from the bulk material. Oxidation, organic contamination, water and electrolytic interaction, protein adsorption and cellular interaction may, therefore, be altered on the surface of such inclusion spots. Unpredictable distributions of inclusions such as those mentioned above provide unpredictable and uncontrolled heterogeneous surface available for interaction with plasma proteins and cells. Specifically, these inclusions interrupt the regular distribution pattern of surface free energy and electrostatic charges on the metal surface that determine the nature and extent of plasma protein interaction. Plasma proteins deposit nonspecifically on surfaces according to their relative affinity for polar or non-polar areas and their concentration in blood. A replacement process known as the Vroman effect, Vroman L., *The importance of surfaces in contact phase reactions, Seminars of Thrombosis and Hemostasis* 1987; 13(1): 79–85, determines a time-dependent sequential replacement of predominant proteins at an artificial surface, starting with albumin, following with IgG, fibrinogen and ending with high molecular weight kininogen. Despite this variability in surface adsorption specificity, some of the adsorbed proteins have receptors available for cell attachment and therefore constitute adhesive sites. Examples are: fibrinogen glycoprotein receptor IIbIIIa for platelets and fibronectin RGD sequence for many blood activated cells. Since the coverage of an artificial surface with endothelial cells is a favorable end-point in the healing process, favoring endothelialization in device design is desirable in implantable vascular device manufacturing.

Normally, endothelial cells (EC) migrate and proliferate to cover denuded areas until confluence is achieved. Migration, quantitatively more important than proliferation, proceeds under normal blood flow roughly at a rate of 25 µm/hr or 2.5 times the diameter of an EC, which is nominally 10 µm. EC migrate by a rolling motion of the cell membrane, coordinated by a complex system of intracellular filaments attached to clusters of cell membrane integrin receptors, specifically focal contact points. The integrins within the focal contact sites are expressed according to complex signaling mechanisms and eventually couple to specific amino acid sequences in substrate adhesion molecules (such as RGD, mentioned above). An EC has roughly 16–22% of its cell surface represented by integrin clusters. Davies, P. F., Robotewskyi A., Griem M. L. *Endothelial cell adhesion in real time. J.Clin.Invest.* 1993; 91:2640–2652, Davies, P. F., Robotewski, A., Griem, M. L., *Qualitiative studies of endothelial cell adhesion, J.Clin.Invest.* 1994; 93:2031–2038. This is a dynamic process, which implies more than 50% remodeling in 30 minutes. The focal adhesion contacts vary in size and distribution, but 80% of them measure less than 6 $\mu m^2$, with the majority of them being about 1 $\mu m^2$, and tend to elongate in the direction of flow and concentrate at leading edges of the cell. Although the process of recognition and signaling to determine specific attachment receptor response to attachment sites is incompletely understood, regular availability of attachment sites, more likely than not, would favorably influence attachment and migration. Irregular or unpredictable distribution of attachment sites, that might occur as a result of various inclusions, with spacing equal or smaller to one whole cell length, is likely to determine alternating hostile and favorable attachment conditions along the path of a migrating cell. These conditions may vary from optimal attachment force and migration speed to insufficient holding strength to sustain attachment, resulting in cell slough under arterial flow conditions. Due to present manufacturing processes, current implantable vascular devices exhibit such variability in surface composition as determined by surface sensitive techniques such as atomic force microscopy, X-ray photoelectron spectroscopy and time-of-flight secondary ion mass spectroscopy.

There have been numerous attempts to increase endothelialization of implanted stents, including covering the stent with a polymeric material (U.S. Pat. No. 5,897,911), imparting a diamond-like carbon coating onto the stent (U.S. Pat. No. 5,725,573), covalently binding hydrophobic moieties to a heparin molecule (U.S. Pat. No. 5,955,588), coating a stent with a layer of blue to black zirconium oxide or zirconium nitride (U.S. Pat. No. 5,649,951), coating a stent with a layer of turbostratic carbon (U.S. Pat. No. 5,387,247), coating the tissue-contacting surface of a stent with a thin layer of a Group VB metal (U.S. Pat. No. 5,607,463), imparting a porous coating of titanium or of a titanium alloy, such as Ti—Nb—Zr alloy, onto the surface of a stent (U.S. Pat. No. 5,690,670), coating the stent, under ultrasonic conditions, with a synthetic or biological, active or inactive agent, such as heparin, endothelium derived growth factor, vascular growth factors, silicone, polyurethane, or polytetrafluoroethylene, U.S. Pat. No. 5,891,507), coating a stent with a silane compound with vinyl functionality, then forming a graft polymer by polymerization with the vinyl groups of the silane compound (U.S. Pat. No. 5,782,908), grafting monomers, oligomers or polymers onto the surface of a stent using infrared radiation, microwave radiation or high voltage polymerization to impart the property of the monomer, oligomer or polymer to the stent (U.S. Pat. No. 5,932,299).

Thus, the problems of thrombogenicity and re-endothelialization associated with stents have been addressed by the art in various manners which cover the stent with either a biologically active or an inactive covering which is less thrombogenic than the stent material and/or which has an increased capacity for promoting re-endothelialization of the stent situs. These solutions, however, all require the use of existing stents as substrates for surface derivatization or modification, and each of the solutions result in a biased or laminate structure built upon the stent substrate. These prior art coated stents are susceptible to delaminating and/or cracking of the coating when mechanical stresses of transluminal catheter delivery and/or radial expansion in vivo. Moreover, because these prior art stents employ coatings applied to stents fabricated in accordance with conventional stent formation techniques, e.g., cold-forming metals, the underlying stent substrate is characterized by uncontrolled heterogeneities on the surface thereof. Thus, coatings merely are laid upon the heterogeneous stent surface, and inherently conform to the topographical heterogeneities in the stent surface and mirror these heterogeneities at the blood contact surface of the resulting coating. This is conceptually similar to adding a coat of fresh paint over an old coating of blistered paint; the fresh coating will conform to the blistering and eventually, blister and delaminate from the underlying substrate. Thus, topographical heterogeneities are typically telegraphed through a surface coating. Chemical heterogeneities, on the other hand, may not be telegraphed through a surface coating but may be exposed due to cracking or peeling of the adherent layer, depending upon the particular chemical heterogeneity.

The current invention entails creating valve flap members and other implantable septa, for example, access ports, of vacuum deposited metal and/or pseudometallic materials. According to a preferred embodiment of the invention, the manufacture of valve flap members and other implantable septa fabricated of metallic and/or pseudometallic films is controlled to attain a regular, homogeneous atomic and molecular pattern of distribution along their fluid-contacting surfaces. This avoids the marked variations in surface composition, creating predictable oxidation and organic adsorption patterns and has predictable interactions with water, electrolytes, proteins and cells. Particularly, EC migration is supported by a homogeneous distribution of binding domains that serve as natural or implanted cell attachment sites, in order to promote unimpeded migration and attachment. Based on observed EC attachment mechanisms such binding domains should have a repeating pattern along the blood contact surface of no less than 1 μm radius and 2 μm border-to-border spacing between binding domains. Ideally, the inter-binding domain spacing is less than the nominal diameter of an endothelial cell in order to ensure that at any given time, a portion of an endothelial cell is in proximity to a binding domain.

SUMMARY OF THE INVENTION

In accordance with the present invention, there is provided an improved film structure for implantable moveable septa, such as valve flaps, access ports, prosthetic ventricular members or similar types of anatomical prosthetic replacements.

It is, therefore, a primary of the present invention to provide a prosthetic unidirectional valve having valve flap members fabricated of biocompatible metal and/or pseudometallic films. The valvular prosthesis of the present invention consists generally of a stent body member, a graft, and valve flaps. The stent body member may be fashioned by laser cutting a hypotube or by weaving wires into a tubular structure, and is preferably made from shape memory or super-elastic materials, such as nickel-titanium alloys known as NITINOL, but may be made of balloon expandable stainless steel or other plastically deformable stent materials as are known in the art, such as titanium or tantalum, or may be self-expanding such as by weaving stainless steel wire into a stressed-tubular configuration in order to impart elastic strain to the wire. The graft is preferably a biocompatible, fatigue-resistant membrane which is capable of endothelialization, and is attached to the stent body member on at least portions of either or both the luminal and abluminal surfaces of the stent body member by suturing to or encapsulating stent struts. The valve leaflets are preferably formed by sections of the graft material attached to the stent body member.

The stent body member is shaped to include the following stent sections: proximal and distal anchors, a intermediate annular stent section, and at least one valve arm or blood flow regulator struts. The proximal and distal anchor sections are present at opposing ends of the prosthesis and subtend either an acute, right or obtuse angle with a central longitudinal axis that defines the cylindrical prosthesis. In either the CV or CC configurations, the proximal anchor is configured to assume approximately a right angle radiating outward from the central longitudinal axis of the prosthesis in a manner which provides an anchoring flange. When being delivered from a delivery catheter, the proximal anchor is deployed first and engages the native tissue and anatomical structures just proximal to the anatomic valve, such as the left ventricle wall in the case of retrograde orthotopic delivery at the aortic valve. Deployment of the proximal anchor permits the intermediate annular stent section to be deployed an reside within the native valve annular space and the abluminal surface of the intermediate annular stent section to abut and outwardly radially compress the anatomic valve leaflets against the vascular wall. The distal anchor is then deployed and radially expands to contact the vascular wall and retain the prosthesis in position, thereby excluding the anatomic valve leaflets from the bloodflow and replacing them with the prosthetic valve leaflets.

Flow regulation in the inventive stent valve prosthesis is provided by the combination of the prosthetic valve leaflets and the valve arms and is biased closed in a manner similar manner to that described for a surgically implanted replacement heart valve by Boretos, U.S. Pat. No. 4,222,126. The valve regulator-struts are preferably configured to be positioned to radiate inward from the stent body member toward the central longitudinal axis of the prosthesis. The graft-leaflet has the appearance of a partially-everted tube where the innermost layer, on the luminal surface of the stent body member, forms the leaflets and the outer-most layer, on the abluminal surface of the stent body member, forms a sealing graft which contacts and excludes the immobilized anatomical valve leaflets. The struts of the stent are encapsulated by the outer graft-membrane. The valve regulator-struts are encapsulated by the inner leaflet-membrane and serve to bias the valve to the closed position. The regulator-struts also prevent inversion or prolapse of the otherwise unsupported leaflet-membrane during increased supra-valvular pressure. The inner leaflet-membrane may also be attached to the outer graft-membrane at points equidistant from the valve strut-arms in a manner analogous to that described for a surgically implanted replacement heart valve by Cox, U.S. Pat. No. 5,824,063. The combination of the thin walled properties of the leaflet-membrane, the one-sided open lumen support of the intermediate annular stent section, the free ends of the valve leaflets, the biasing and support provided by the valve regulator-struts and the attachment points all work to provide a prosthetic valvular device capable of endoluminal delivery which simulates the hemodynamic properties of a healthy anatomical cardiac or venous valve.

In accordance with another embodiment of the invention, there is provided an implantable valvular prosthesis having a graft covering and valve flap members that are each formed as discrete laminated films of a biocompatible metal or pseudometal. A plurality of openings is provided which pass transversely through the graft member. The plurality of openings may be random or may be patterned. It is preferable that the size of each of the plurality of openings be such as to permit cellular migration through each opening, without permitting fluid flow there through. In this manner, blood cannot flow through the plurality of openings, but various cells or proteins may freely pass through the plurality of openings to promote graft healing in vivo.

Finally, in accordance with the present invention, there is provided an implantable valvular prosthesis having valve flap members and a covering graft member that are fabricated from metallic and/or pseudometallic films that present a blood or tissue contact surface that is substantially homogeneous in material constitution.

DETAILED DESCRIPTION OF THE PREFERRED EMBODIMENTS

Figure 1:
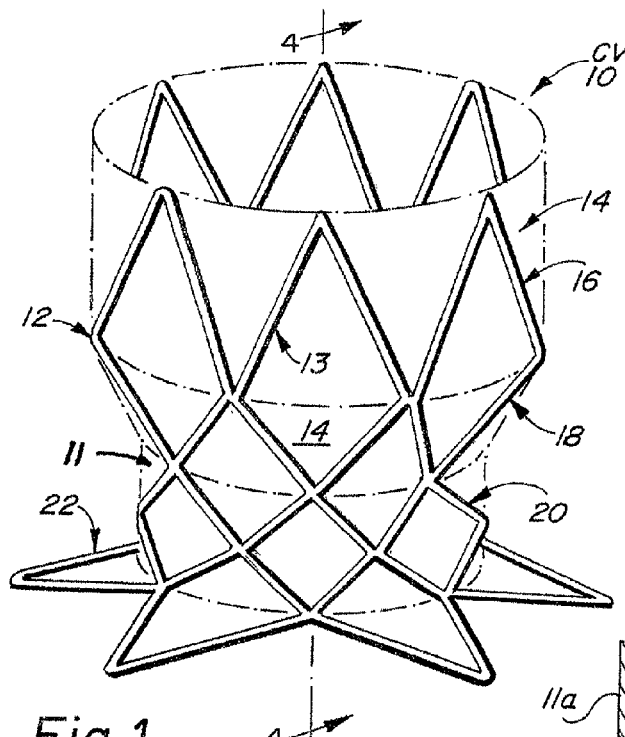
FIG. 1 is a perspective view of the inventive valve stent chamber-to-vessel embodiment in its fully deployed state.
Figure 3:
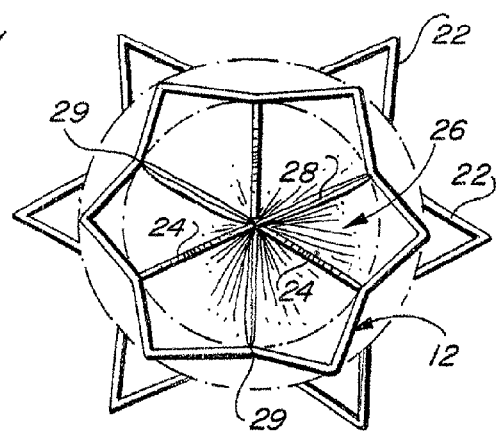
FIG. 3 is a top view of the inventive valve stent chamber-to-vessel embodiment in its fully deployed state.

The present invention consists generally of three preferred embodiments, each embodiment corresponding to a prosthetic stent valve configuration adapted for either heart chamber to blood vessel communication, chamber to chamber communication or vessel to vessel, or intravascular configuration. Certain elements are common to each of the preferred embodiments of the invention, specifically, each embodiment includes a stent body member which defines a central annular opening along the longitudinal axis of the stent body member, a graft member which covers at least a portion of the stent body member along either the luminal or abluminal surfaces of the stent body member, at least one biasing arm is provided and projects from the stent body member and into the central annular opening of the stent body member, and at least one valve flap member which is coupled to each biasing arm such that the biasing arm biases the valve flap member to occlude the central annular opening of the stent body member under conditions of a zero pressure differential across the prosthesis. The stent body member is preferably made of a shape memory material or superelastic material, such as NITINOL, but also is fabricated from either plastically deformable materials or spring-elastic materials such as are well known in the art. Additionally, the stent body member has three main operable sections, a proximal anchor section, a distal anchor section and an intermediate annular section which is intermediate the proximal and distal anchor sections. Depending upon the specific inventive embodiment, the distal and proximal anchor sections may be either a diametrically enlarged section or may be a flanged section. The intermediate annular section defines a valve exclusion region and primary blood flow channel of the inventive valve stent. The intermediate annular section defines a luminal opening through which blood flow is established. The transverse cross-section of the luminal opening may be circular, elliptical, ovular, triangular or quadralinear, depending upon the specific application for which the valve stent is being employed. Thus, for example, where a tricuspid valve is particularly stenosed, it may be preferable to employ a valve stent with a luminal opening in the intermediate annular section which has a triangular transverse cross-sectional dimension.

In each of the foregoing embodiments, the graft member and the valve flap members are fabricated of a biocompatible metal and/or a biocompatible pseudometal and are formed as films of material that are preferably laminated to enhance their material properties. The metal films may be micro or nanoporous to enhance endothelialization as described in greater detail in parent patent application U.S. Ser. No. 09/853,985 filed May 11, 2001, which is hereby incorporated by reference. Suitable materials to fabricated the inventive graft and valve flap members are chosen for their biocompatibility, mechanical properties, i.e., tensile strength, yield strength, and their ease of deposition include, without limitation, the following: titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel. The graft member and the valve flap members are formed by vacuum deposition methodologies.

Chamber-to-Vessel Configuration

An implantable prosthesis or prosthetic valve in accordance with certain embodiments of the chamber-to-vessel CV configuration of the present invention is illustrated generally in FIGS. 1–5. The chamber-to-vessel valve stent 10 consists of an expandable stent body member 12 and graft member 11. The stent body member 12 is preferably made from a shape memory and/or superelastic NITINOL material, or thermomechanically similar materials, but may be made of plastically deformable or elastically compliant materials such as stainless steel, titanium or tantalum. The graft member 11 is fabricated of biocompatible metal and/or pseudometallic materials, such as thin film stainless steel, nickel-titanium alloy, tantalum, titanium or carbon fiber. The stent body member 12 is configured to have three functional sections: a proximal anchor flange 22, an intermediate annular section 20 and a distal anchor section 16. The stent body member 12, as with conventional stents is formed of a plurality of stent struts 13 which define interstices 14 between adjacent stent struts 13. The stent body member preferably also includes a transitional section 18 that interconnects the intermediate annular section 20 and the distal anchor section 16, which together define a valve exclusion region of the inventive stent valve 10 to exclude the anatomic valve after implantation. The proximal anchor flange 22, the intermediate annular section 20 and the distal anchor section 16 are each formed during the formation of the stent body member and are formed from the same material as the stent body member and comprise stent struts 13 and intervening interstices 14 between adjacent pairs of stent struts 13. The anchor flange 22, for example, consists of a plurality of stent struts and a plurality of stent interstices, which project radially outwardly away from the central longitudinal axis of the stent body member. Thus, the different sections of the stent body member 12 are defined by the positional orientation of the stent struts and interstices relative to the central longitudinal axis of the stent body member 12.

Figure 2:
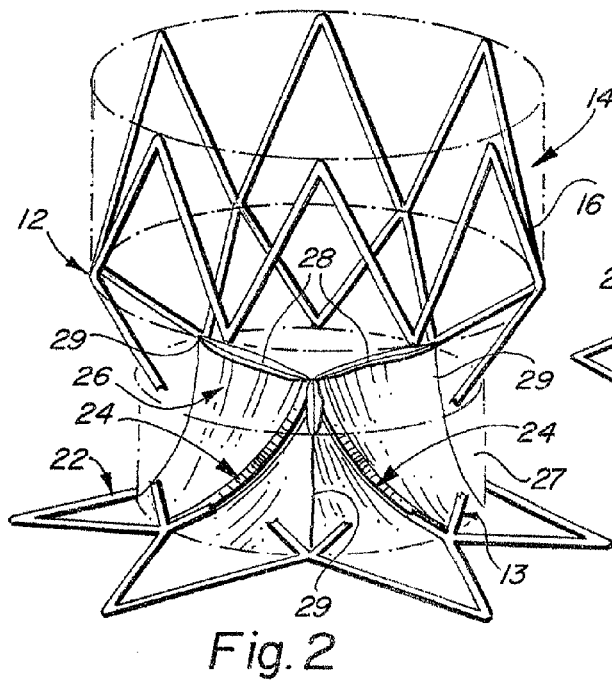
FIG. 2 is a perspective view of the inventive valve stent chamber-to-vessel embodiment in its fully deployed state with the outermost graft layer and stent layer partially removed to show an embodiment of the valve apparatus.
Figure 5:
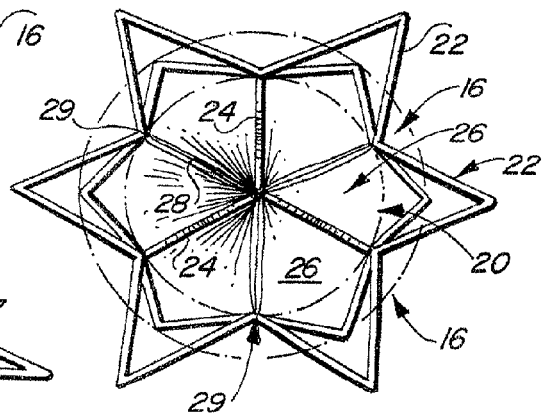
FIG. 5 is a bottom view of the inventive valve stent chamber-to-vessel embodiment in its fully deployed state.

With reference to FIG. 2, there is shown in greater detail the valve body 26 and valve arms or flow regulator struts 24 coupled to the stent body member 12. The valve body 26 subtends the central annular opening of the stent valve 10 and is illustrated in its closed position. In accordance with one embodiment of the present invention, the graft member 11 consists of an outer or abluminal graft member 11a and an inner or luminal graft member 11b. The outer graft member 11a encloses at least a portion of the abluminal surface of the intermediate annular section 20 of the stent body member, while the inner graft member 11b is coupled, on the luminal surface of the intermediate annular section 20 of the stent body member 12, to the outer graft member 11a through the interstices 14 of the stent body member. The valve body 26 is formed by everting the inner graft member 11b toward the central longitudinal axis of the stent body member 12 such that free ends or valve flap portions 28 of the inner graft member 11b are oriented toward the distal anchor section 16 of the stent body member 12 and a pocket or envelope 27 is formed at the eversion point of the inner graft member 11b adjacent the junction between the intermediate annular section 20 and the proximal anchor flange 22 of the stent body member 12. Alternatively, portions of the outer graft member 11a may be passed through to the luminal surface of the stent body member 12, thereby becoming the inner graft member 11b and everted to form the valve body 26.

Valve arms or regulator struts 24 are coupled or formed integral with the stent body member 12 and are positioned adjacent the junction point between intermediate annular section 20 and the proximal anchor flange 22 of the stent body member 12. The valve arms 24 are oriented radially inward toward the central longitudinal axis of the stent body member 12 when in their zero strain state. The valve arms 24 are attached or coupled to the valve flap portions 28 of the inner graft member leaflets to bias the valve flap portions 28 to the closed position when under zero pressure differential across the stent valve 10.

Figure 4:
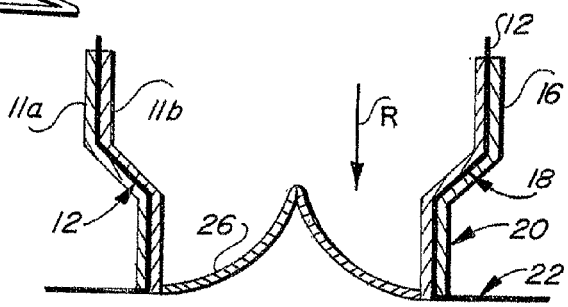
FIG. 4 shows the cross-sectional taken along line 4—4 of FIG. 1.

The zero strain position of the valve arms 24 is radially inward and orthogonal to the central longitudinal axis of the stent valve 10. Valve arms 24 have a length which is preferably longer than the radius of the luminal diameter of the stent valve 10, and they extent distally into the lumen of the stent valve 10 such that, in conjunction with the action of the valve leaflets 28, the valve arms 24 are prevented from achieving their zero strain configuration thereby biasing the valve closed. As shown in FIG. 4, the valve arms 24 force the valve leaflets 28 to collapse into the center of the lumen of the stent valve 10, thus biasing the valve to its closed position.

It is preferable to couple sections of the valve flaps 28, along a longitudinal seam 29, to the inner graft member 11b and the outer graft member 11a at points equidistant from the valve arms 24 in order to impart a more cusp-like structure to the valve flaps 28. It should be appreciated, that the graft member 11 should cover at least a portion of the abluminal surface of the stent body member 12 in order to exclude the anatomic valves, but may also cover portions or all of the stent valve member 12, including the distal anchor section 16, the intermediate annular section 20, the transition section 18 and/or the proximal anchor flange 22, on either or both of the luminal and abluminal surfaces of the stent body member.

In accordance with a particularly preferred embodiment of the CV valve stent 10, the proximal anchor flange 22, which consists of a plurality of stent struts and stent interstices which project radially outward away from the central longitudinal axis of the valve stent 10, is configured to have one or more stent struts eliminated from the proximal anchor flange 22 to define an open region which is positioned in such a manner as to prevent the CV valve stent 10 from interfering with or impinging upon an adjacent anatomic structure. For example, where the CV valve stent 10 is to be an aortic valve prosthesis, it is known that the mitral valve is immediately adjacent the aortic valve, and the mitral valve flaps deflect toward the left ventricle. Thus, placing the CV valve stent 10 such that the proximal anchor flange 22 is adjacent the mitral valve might, depending upon the particular patient anatomy, interfere with normal opening of the mitral valve flaps. By eliminating one or more of the stent struts in the proximal anchor flange 22, an opening is created which permits the mitral valve flaps to deflect ventricularly without impinging upon the proximal anchor flange 22 of the CV valve stent 10.

Similarly, the stent struts of the CV valve stent 10 may be oriented in such a manner as to create interstices of greater or smaller area between adjacent struts, to accommodate a particular patient anatomy. For example, where the stent struts in the distal anchor section 16 would overly an artery branching from the aorta, such as the coronary ostreum arteries, it may be desirable to either eliminate certain stent struts, or to configure certain stent struts to define a greater interstitial area to accommodate greater blood flow into the coronary ostreum.

In the case of providing an oriented opening in the proximal anchor flange, or an oriented opening in the interstitial spaces of the distal anchor, it is desirable to provide radiopaque markers on the stent body member 12 to permit the CV valve stent to be oriented correctly relative to the anatomic structures.

Figure 6A:
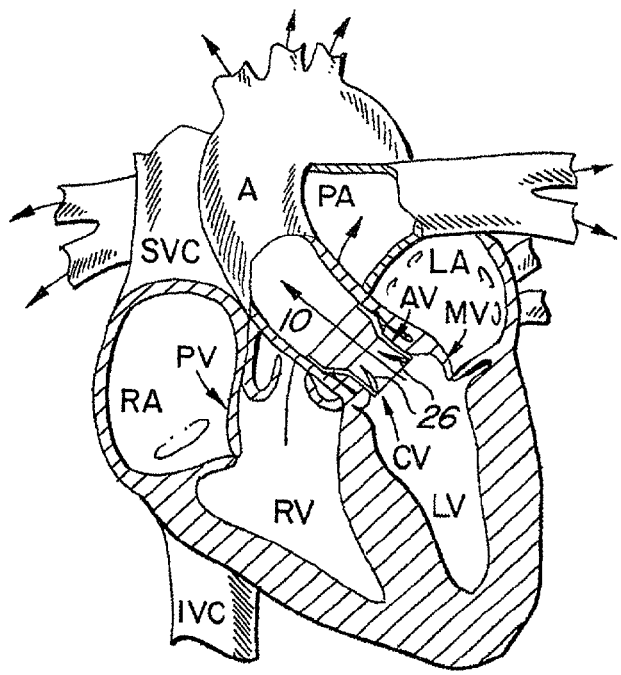
FIG. 6A illustrates a cross-sectional view of a human heart during systole with the inventive valve stent chamber-to-vessel embodiment implanted in the aortic valve and illustrating a blood flow vector of an ejection fraction leaving the left ventricle and passing through the inventive valve stent.
Figure 6B:
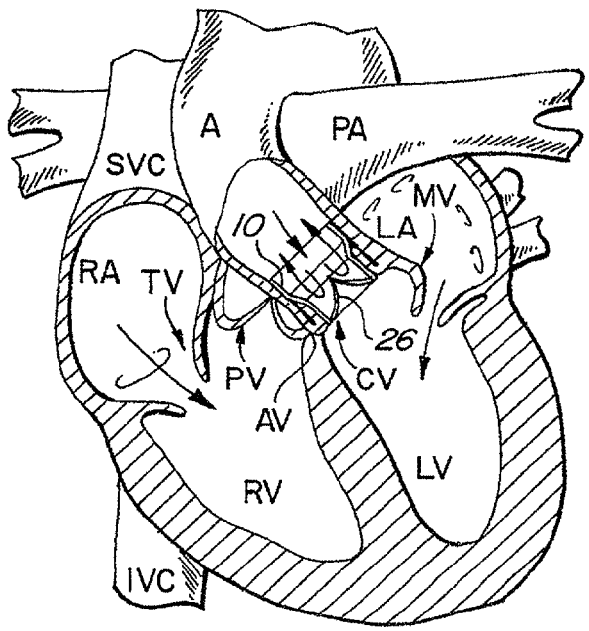
FIG. 6B illustrates a cross-sectional view of a human heart during diastole with the inventive valve stent chamber-to-vessel embodiment implanted in the aortic valve and illustrating a blood flow vector of blood passing from the left atrium, through the mitral valve and into the left ventricle during and a retrograde blood flow vector blocked by the inventive valve stent in the aorta.

FIGS. 6A and 6B illustrate the inventive CV stent valve 10 implanted in the position of the aortic valve and excluding the anatomic aortic valve AV. FIG. 6A illustrates the heart during systole in which a positive pressure is applied to the prosthetic aortic valve by contraction of the left ventricle LV and the ejection fraction represented by the arrow. The systolic pressure overcomes the bias exerted by the valve arms 24 and causes the valve leaflets 26 to open and release the ejection fraction into the aorta. FIG. 6 B illustrates that the presence of a negative pressure head across the stent valve 10, i.e. such as that during diastole, causes the biased valve leaflets 26 which are already closed, to further close, and prevent regurgitation from the aorta into the left ventricle.

Chamber-to-Chamber Configuration

FIGS. 7–11 illustrate the inventive stent valve in the chamber-to-chamber (CC) configuration 40. The CC valve stent 40 is constructed in a manner which is virtually identical to that of the CV valve stent 10 described above, except that the distal anchor section 16 of the CV valve stent 10 is not present in the CC valve stent 40, but is substituted by a distal anchor flange 42 in the CC stent valve. Thus, like the CV valve stent 10, described above, the CC valve stent 40 if formed of a stent body member 12 and a graft member 11, with the graft member having luminal 11b and abluminal 11a portions which cover at least portions of the luminal and abluminal surfaces of the stent body member 12, respectively. The CC valve stent 40 has both a proximal anchor flange 44 and a distal anchor flange 42 which are formed of sections of the stent body member 12 which project radially outward away from the central longitudinal axis of the CC valve stent 40 at opposing ends of the stent body member 12.

Like the CV valve stent 10, the luminal graft portion 11b is everted inwardly toward the central longitudinal axis of the valve stent 40 and free ends 28 of the luminal graft portion 11b to form valve flaps 26 which project distally toward distal anchor flange 42. Flow regulation struts 24 are coupled to or integral with the proximal anchor flange 44 and intermediate annular section 20 and project radially inward toward the central longitudinal axis of the CC valve stent 40. The valve flaps 26 are coupled to the flow regulation struts 24 and the flow regulation struts 24 bias the valve flaps 26 to a closed position under a zero strain load.

Like with the CV stent valve 10, it is preferable to couple sections of the valve flaps 28, along a longitudinal seam 29, to the inner graft member 11b and the outer graft member 11a at points equidistant from the valve arms 24 in order to impart a more cusp-like structure to the valve flaps 28.

Figure 12A:
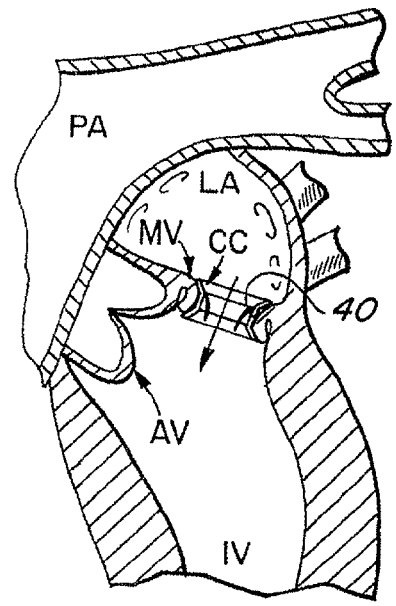
FIG. 12A illustrates a cross-sectional view of a human heart during atrial systole with the inventive valve stent chamber-to-chamber embodiment implanted at the site of the mitral valve and illustrating a blood flow vector of a filling fraction leaving the left atrium and entering the left ventricle.
Figure 12B:
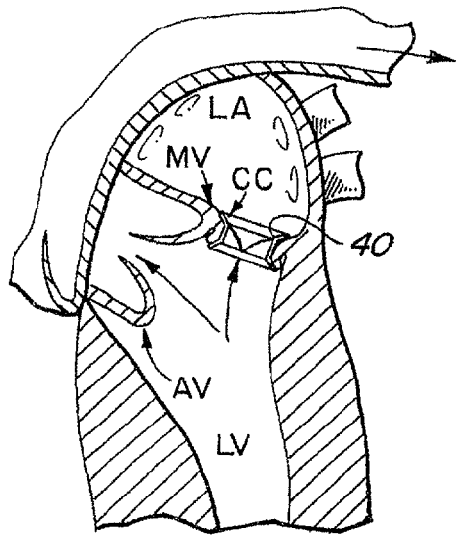
FIG. 12B illustrates a cross-sectional view of a human heart during atrial diastole with the inventive valve stent chamber-to-chamber embodiment implanted at the site of the mitral valve and illustrating a blood flow vector of an ejection fraction from the left ventricle to the aorta and the back pressure against the implanted mitral valve prosthesis.
Figure 7:
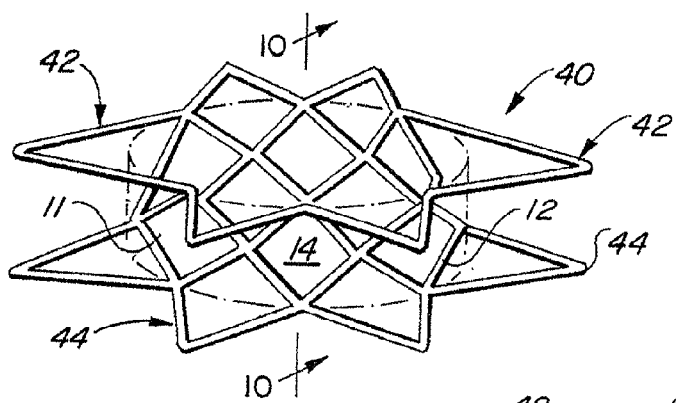
FIG. 7 is a perspective view of the inventive valve stent chamber-to-chamber embodiment in its fully deployed state.
Figure 8:
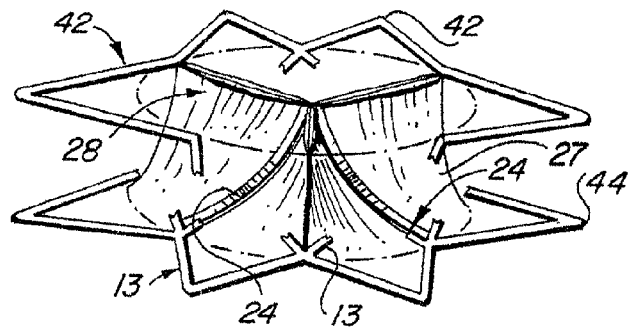
FIG. 8 is a is a perspective view of the inventive valve stent chamber-to-chamber embodiment in its fully deployed state with the outermost graft layer and stent layer partially removed to show an embodiment of the valve apparatus.
Figure 9:
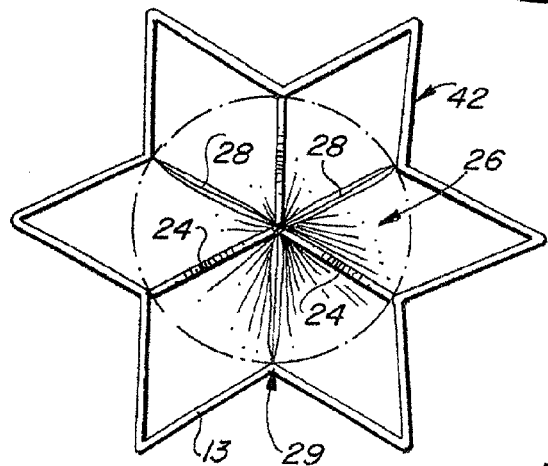
FIG. 9 is a top view of the inventive valve stent chamber-to-chamber embodiment in its fully deployed state.
Figure 10:
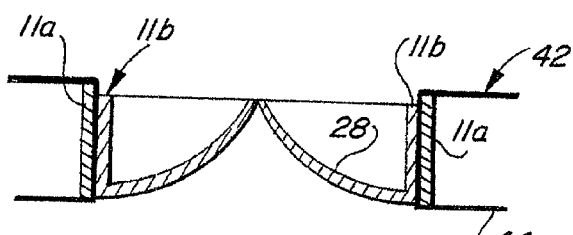
FIG. 10 shows the cross sectional view taken along line 10—10 of FIG. 7.
Figure 11:
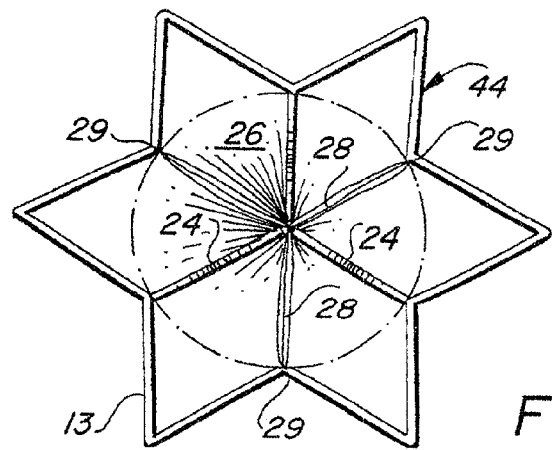
FIG. 11 is a bottom view of inventive valve stent chamber-to-chamber embodiment in its fully deployed state.
Figure 13:
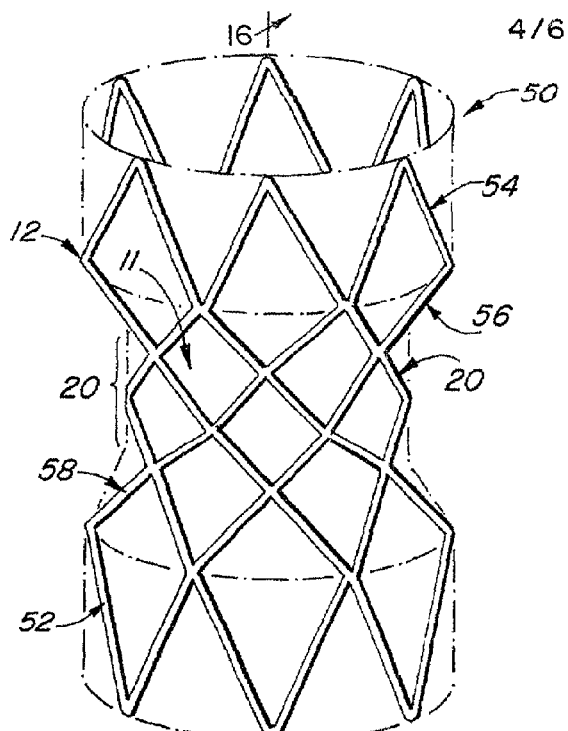
FIG. 13 is a perspective view of the chamber-to-vessel configuration in the fully deployed state.
Figure 15:
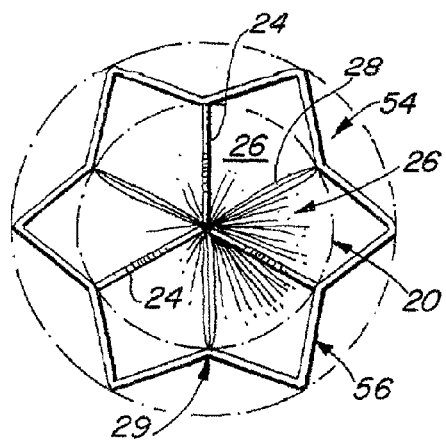
FIG. 15 is a top view of the same configuration.
Figure 14:
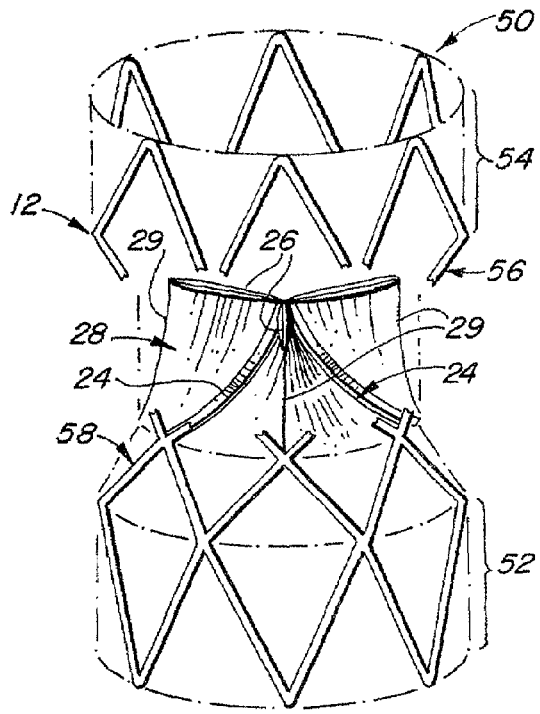
FIG. 14 is a perspective view of the same configuration in the fully deployed state with the outermost graft layer and stent layer partially removed to show an embodiment of the valve apparatus.
Figure 16:
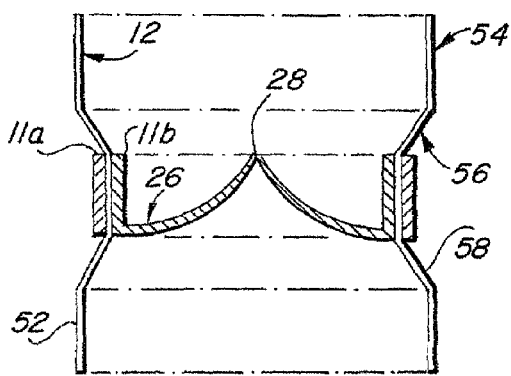
FIG. 16 shows the cross sectional view of the same configuration for the deployed state.
Figure 17:
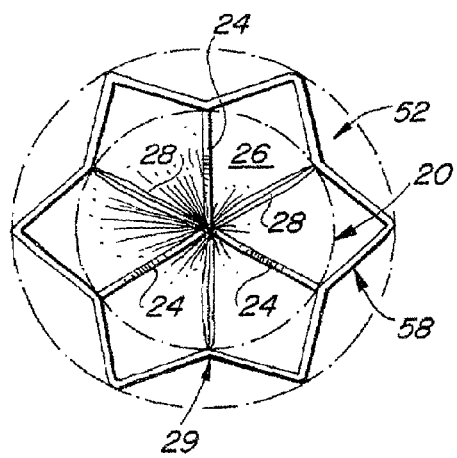
FIG. 17 is a bottom view of the same configuration.

Turning to FIGS. 12A and B there is illustrated the inventive CC stent valve 40 implanted in the position of the mitral valve and excluding the anatomic mitral valve MV. FIG. 12A illustrates the heart during atrial systole in which a positive pressure is applied to the prosthetic mitral valve by contraction of the left atrium LA and the pressure exerted by the blood flow represented by the arrow. The atrial systolic pressure overcomes the bias exerted by the valve arms 24 onto the valve leaflets 26, and causes the valve leaflets 26 to open and release the atrial ejection fraction into the left ventricle. FIG. 12B illustrates that the presence of a negative pressure head across the stent valve 40, i.e. such as that during atrial diastole, causes the biased valve leaflets 26 which are already closed, to further close, and prevent backflow from the left ventricle into the left atrium.

In accordance with another preferred embodiment of the invention, the CC configuration may be adapted for use in repairing septal defects. By simply substituting a membrane for the valve leaflets 26, the lumen of the stent body member 12 is occluded. The CC stent valve 40 may be delivered endoluminally and placed into a position to subtend a septal defect and deployed to occlude the septal defect.

Vessel-to-Vessel Configuration

Turning now to FIGS. 13–17, there is illustrated the inventive stent valve in its vessel-to-vessel (VV) valve stent configuration 50. The VV valve stent 50 is constructed in a manner which is virtually identical to that of the CV valve stent 10 described above, except that the proximal anchor flange 22 of the CV valve stent 10 is not present in the VV valve stent 50, but is substituted by a proximal anchor section 52 in the VV stent valve. Thus, like the CV valve stent 10, described above, the VV valve stent 50 is formed of a stent body member 12 and a graft member 11, with the graft member having luminal 11b and abluminal 11a portions which cover at least portions of the luminal and abluminal surfaces of the stent body member 12, respectively. The VV valve stent 50 has both a proximal anchor section 52 and a distal anchor section 54 which are formed of sections of the stent body member 12 which are diametrically greater than the intermediate annular section 20 of the VV valve stent 50. Transition sections 56 and 58 taper outwardly away from the central longitudinal axis of the VV valve stent 50 and interconnect the intermediate annular section 20 to each of the distal anchor section 54 and the proximal anchor section 52, respectively.

Like the CV valve stent 10, in the VV valve stent 50, the graft member 11, particularly the luminal graft portion 11b or the abluminal graft portion 11a, or both, is everted inwardly toward the central longitudinal axis of the valve stent 40 and free ends 28 of the luminal graft portion 11b to form valve flaps 26 which project distally toward distal anchor flange 42. Flow regulation struts 24 are coupled to or integral with the stent body member at the proximal transition section 58 and project radially inward toward the central longitudinal axis of the VV valve stent 50. The valve flaps 26 are coupled to the flow regulation struts 24 and the flow regulation struts 24 bias the valve flaps 26 to a closed position under a zero strain load. Like with the CV stent valve 10 and the CC stent valve 40, it is preferable to couple sections of the valve flaps 28, along a longitudinal seam 29, to the inner graft member 11b and the outer graft member 11a at points equidistant from the valve arms 24 in order to impart a more cusp-like structure to the valve flaps 28.

Figure 18A:
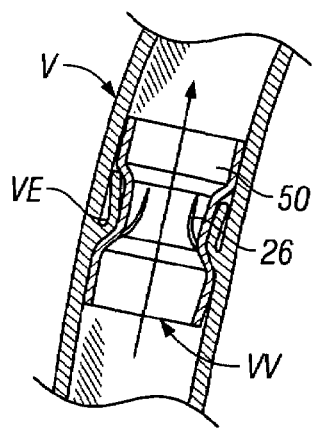
FIG. 18A and 18B show cross-sectional views of a vein and venous valve illustrating the inventive prosthetic venous valve in the open and closed state.
Figure 18B:
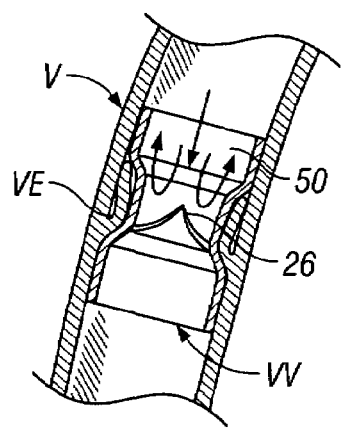

Turning to FIGS. 18A and B there is illustrated the inventive VV stent valve 50 implanted in the position of a venous valve and excluding the anatomic venous valve flaps VE. FIG. 18A illustrates the vein under systolic blood pressure in which a positive pressure is applied to the prosthetic venous valve and the pressure exerted by the blood flow represented by the arrow. The systolic pressure overcomes the bias exerted by the valve arms 24 onto the valve leaflets 26, and causes the valve leaflets 26 to open and permit blood flow through the prosthesis. FIG. 18B illustrates that the presence of a negative pressure head across the VV stent valve 50, i.e. such as which exists at physiological diastolic pressures, causes the biased valve leaflets 26 which are already closed, to further close, and prevent backflow from the left ventricle into the left atrium.

The purpose of the proximal 54 and distal 52 anchor sections of the stent body member 12 is to anchor the prosthesis at the anatomic vessel-vessel junction, such as a venous valve, while causing minimal interference with adjacent tissue. The intermediate annular section 20 of the VV stent valve 50 excludes diseased anatomic leaflets and surrounding tissue from the flow field. The flare angle of the transition sections 56, 58 between the intermediate annular section 20 and each of the proximal and distal anchor sections 54, 52, respectively, may be an acute angle, a right angle or an obtuse angle, depending upon the anatomical physiological requirements of the implantation site. Alternatively, the transition sections 56, 58 may be coplanar with the proximal and distal anchor section 52, 54, respectively, thereby, eliminating any transition flare angle, depending upon the anatomical and physiological requirements of the delivery site.

Figure 19:
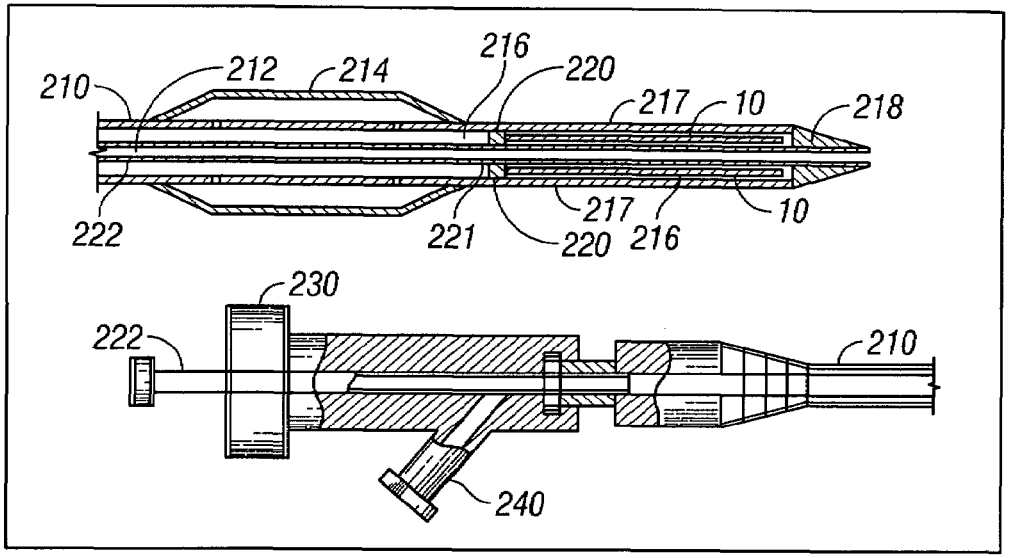
FIGS. 19 is a cross-sectional diagrammatic view of a valvuloplasty and stent valve delivery catheter in accordance with the present invention.

Single Catheter Valvuloplasty Stent Valve Delivery System and Method of Delivery In accordance with the present invention, there is also provide a single catheter valvuloplasty and valve stent delivery system 200 illustrated in FIG. 19. The objective of the single catheter delivery system 200 is to permit the surgeon or interventionalist to percutaneously deliver and deploy the inventive valve stent 10, 40 or 50 at the desired anatomical site and to perform valvuloplasty with a single catheter. In accordance with the preferred embodiment of the single catheter delivery system 200 of the present invention, there is provided a catheter body 210 having dual lumens 212, 216. A first lumen 212 is provided as a guidewire lumen and is defined by a guidewire shaft 222 that traverses the length of the catheter body 210. A second lumen is an inflation lumen 216 for communicating an inflation fluid, such as saline, from an external source, through an inflation port 240 at the operator end of the catheter 210, to an inflatable balloon 214 located at or near the distal end of the catheter body 210. The inflation lumen 216 is defined by an annular space between the luminal surface of the catheter body 210 and the abluminal surface of the guidewire shaft 222. A capture sheath 217 is provided at the distal end 215 of the catheter body 210 and is positioned adjacent and distal the balloon 214. The capture sheath 217 defines an annular space about the guidewire lumen 212 and the capture sheath 217 into which the stent valve 10, 40 or 50 is positioned and retained during delivery. An annular plug member 220 is within the inflation lumen 216 distal the balloon 214 and terminates the inflation lumen 216 in a fluid tight manner. Annular plug member 220 has a central annular opening 221 through which the guidewire shaft 222 passes. The annular plug member 220 is coupled to the guidewire shaft 222 and is moveable axially along the central longitudinal axis of the catheter 200 by moving the guidewire shaft 222. The annular plug member 220 also serves to abut the stent valve 10, 40 and 50 when the stent valve 10, 40 and 50 is positioned within the capture sheath 217. The guidewire shaft 222 passes through the capture sheath 217 and terminates with an atraumatic tip 218 which facilitates endoluminal delivery without injuring the native tissue encountered during delivery. With this configuration, the stent valve is exposed by proximally withdrawing the catheter body 210, while the guidewire shaft 222 is maintained in a fixed position, such that the annular plug member 220 retains the position of the stent valve as it is uncovered by capture sheath 217 as the capture sheath 217 is being proximally withdrawn with the catheter body 210.

In many cases the anatomic valve will be significantly stenosed, and the valve flaps of the anatomic valve will be significantly non-compliant. The stenosed valves may be incapable of complete closure permitting blood regurgitation across the anatomic valve. Thus, it may be desirable to configure the inflatable balloon 214 to assume an inflation profile which is modeled to maximally engage and dilatate the anatomic valves. For example, a tricuspid valve, such as the aortic valve may stenose to an opening which has a generally triangular configuration. In order to maximally dilatate this triangular opening, it may be desirable to employ a balloon profile which assumes a triangular inflation profile. Alternatively, it may be advantageous to configure the balloon such that it does not fully occlude the anatomic lumen when inflated, but permits a quantum of blood flow to pass around the balloon in its inflated state. This may be accomplished by providing channels or ridges on the abluminal surface of the balloon. Additionally, irregular inflation profiles of the balloon may facilitate continuous blood flow about the inflated balloon. Furthermore, it may be desirable to configure the balloon to have an hour-glass inflation profile to prevent migration or slippage of the balloon in the anatomic valve during valvuloplasty.

In accordance with the present invention, it is preferable that the capture sheath 217 be made of a material which is sufficiently strong so as prevent the stent valve 10, 40, 50 from impinging upon and seating into the capture sheath 217 due to the expansive pressure exerted by the stent valve 10, 40, 50 against the capture sheath. Alternatively, the capture sheath 217 may be lined with a lubricious material, such as polytetrafluoroethylene, which will prevent the capture sheath 217 from exerting drag or frictional forces against the stent valve during deployment of the stent valve.

In accordance with the present invention, it is also contemplated that the position of the balloon 214 and the capture sheath 217 may be reversed, such that the balloon 214 is distal the capture sheath 217. In this configuration, the anatomic valve may be radially enlarged by dilatating the balloon 214, then the catheter moved distally to position the capture sheath 217 at the anatomic valve and deployed in the manner described above. This would also allow for post-deployment balloon expansion of the deployed stent valve without the need to traverse the prosthetic valve in a retrograde fashion. Alternatively, the catheter 200 of the present invention may be provided without a balloon 214 in those cases where valvuloplasty is not required, e.g., where a stenotic valve does not need to be opened such as with a regurgitating valve, and the catheter 200 is terminated at its distal end with only a capture sheath 217, and deployment occurs as described above.

Figure 20A:
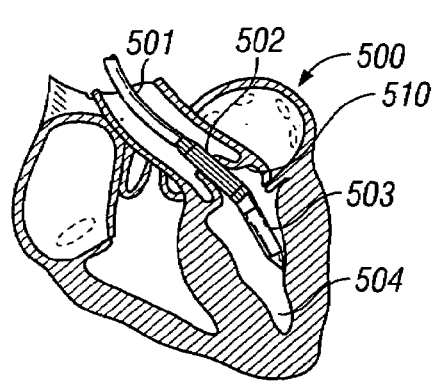
FIG. 20A–20I are diagrammatic cross-sectional views illustrating single catheter valvuloplasty, inventive stent valve delivery and stent valve operation in situ in accordance with the method of the present invention.
Figure 20B:
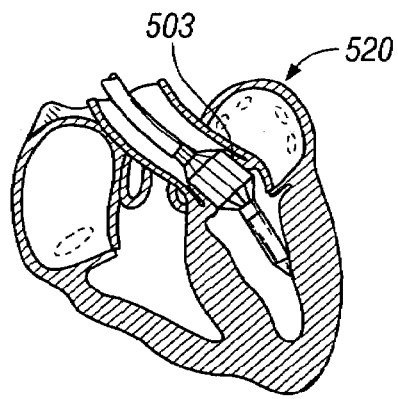
Figure 20C:
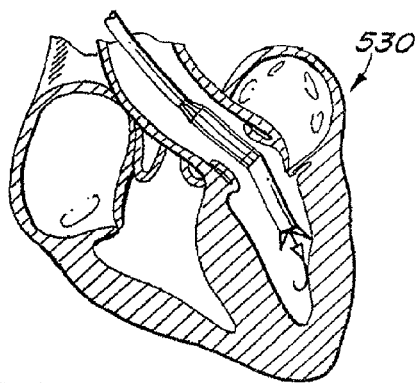
Figure 20D:
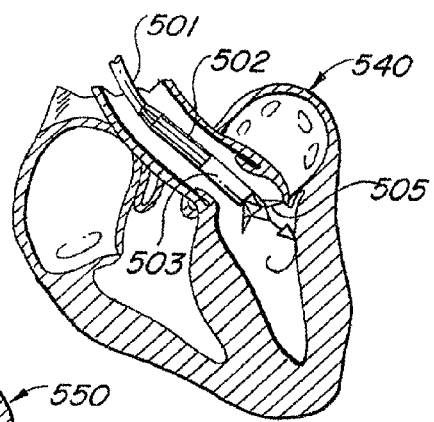
Figure 20E:
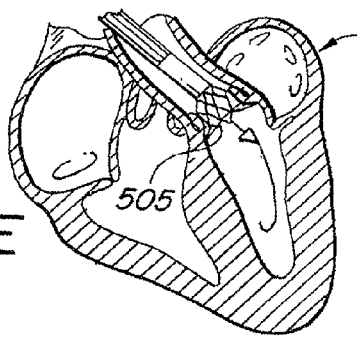
Figure 20F:
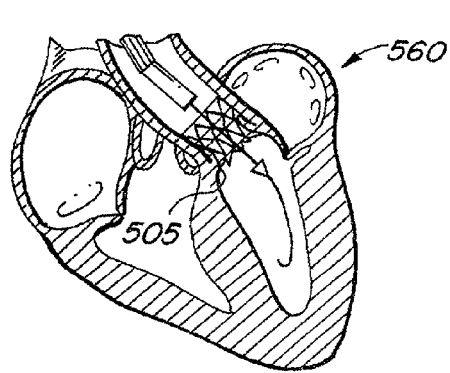
Figure 20G:
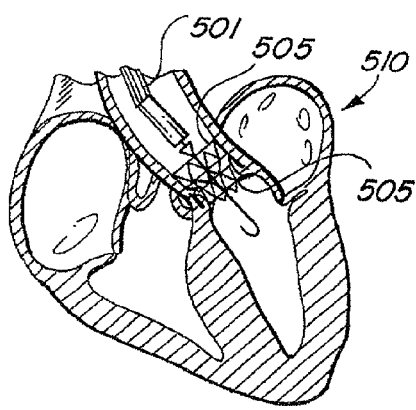
Figure 20H:
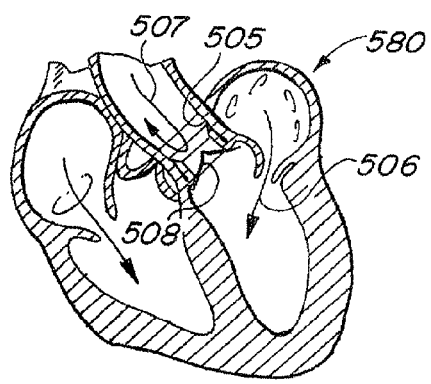
Figure 20I:
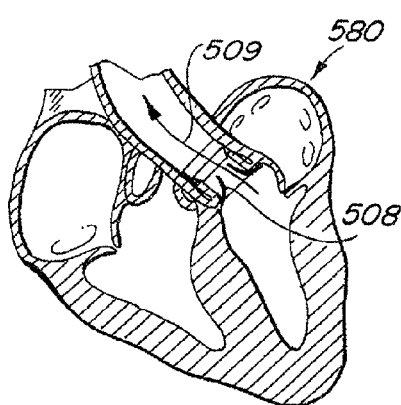

Turning now to FIGS. 20A–20I there is illustrated the sequence of steps in delivery of the stent valve of the present invention, valvuloplasty of the aortic valve and deployment of the stent valve at the position of the aortic valve. The single catheter delivery system 501 having a distal balloon 502 and a capture sheath 503 covering the valve stent 10 (not shown in FIGS. 20A–B), is delivered percutaneously either through a femoral or subclavian artery approach, and traverses the aorta and is passed through the aortic valve 510 such that the balloon 503 on the distal end of catheter 501 is adjacent the aortic valve 510 and the capture sheath 503 is within the left ventricle 504. A valvuloplasty step 520 is performed by inflating balloon 503 to dilate the aortic valve and deform the aortic valve flaps against the aorta wall adjacent the aortic valve. After the valvuloplasty step 520, delivery of the valve stent 505 is initiated by stabilizing the guidewire shaft (not shown) while the catheter body is withdrawn antegrade relative to the blood flow until the proximal anchor flange section of the valve stent 505 is exposed by the withdrawal of the capture sheath 503. The distal anchor flange of the valve stent 505 is then positioned at the junction between the aortic valve and the left ventricle at step 540, such that the distal anchor flange engages the ventricular surface of the aortic valve. The valve stent is fully deployed at step 550 by retrograde withdrawal of the catheter body 501 which continues to uncover the intermediate annular section of the valve stent and release the aortic valve stent 505. at the aortic valve site 510. In step 560, the valve stent 505 is completely deployed from the catheter 501 and the capture sheath 503. The distal anchor section of the valve stent 505 expands and contacts the luminal wall of the aorta, immediately distal the aortic valve, thereby excluding the aortic valve flaps from the lumen of the prosthetic aortic valve stent 505. In step 570, the atraumatic tip and guidewire are retracted by retrograde movement of the guidewire shaft of the catheter, and the catheter 501 is withdrawn from the patient. FIGS. 20H and 20I depict the implanted valve stent 505 during diastole and systole, respectively. During ventricular diastole 580, the left ventricle expands to draw blood flow 506 from the left atrium into the left ventricle. A resultant negative pressure gradient is exerted across the valve stent 505, and the valve arms and valve flaps 506 of the valve stent 505 are biased to the closed position to prevent a regurgitation flow 507 from passing through the valve stent 505 and into the left ventricle 504. During ventricular systole 590, the left ventricle contracts and exerts a positive pressure across the valve stent 505, which overcomes the bias of the valve arms and valve flaps, which open 508 against the luminal wall of the intermediate annular section of the valve stent and permit the ejection fraction 509 to be ejected from the left ventricle and into the aorta.

The method for delivery of the CC valve stent 40 or the VV valve stent 50 is identical to that of the CV stent 10 depicted in FIGS. 20A–20I, except that the anatomical location where delivery and deployment of the valve stent occurs is, of course, different.

Thus, while the present invention, including the different embodiments of the valve stent, the delivery and deployment method and the single catheter valvuloplasty and delivery system, have been described with reference to their preferred embodiments, those of ordinary skill in the art will understand and appreciate that the present invention is limited in scope only by the claims appended hereto.

What is claimed is:

1. An implantable prosthesis having a stent body at least partially covered by a graft member, the graft member forming at least one valve flap member within the stent body, the at least one valve flap member being biased towards a closed position; wherein the graft member and the at least one valve flap member is comprised of a monolithic film layer having a substantially uniform thickness of biocompatible material selected from the group consisting of metals and pseudometals.

2. The implantable prosthesis according to claim 1, wherein the biocompatible material further comprises a plurality of layers.

3. The implantable prosthesis according to claim 1, wherein the biocompatible material is selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

4. The implantable prosthesis according to claim 1, wherein the plurality of valve flap members are extensive from the graft member.

5. The implantable prosthesis according to claim 4, wherein the plurality of valve flap members are formed from a portion of the graft member.

6. An implantable valvular prosthesis having a stent body at least partially covered by a graft member, a biasing arm projecting from the stent body and into a central lumen of the stent body, at least one valve flap member formed from a terminal portion of the graft member, the biasing arm being coupled to the at least one valve flap member and biasing the at least one valve flap member towards a closed position within the central lumen of the stent body; wherein the graft member and the at least one valve flap member are fabricated of a biocompatible film fabricated of a material selected from metals and pseudometals.

7. The implantable valvular prosthesis according to claim 6, wherein the biocompatible film further comprises a plurality of film layers.

8. An implantable valvular prosthesis, comprising a generally tubular stent body having a central lumen, a generally tubular graft member, a plurality of valve flap members, each being fabricated out of a biocompatible material selected from the group consisting of metals and pseudometals; wherein the graft member is concentrically disposed relative to the generally tubular stent body and the plurality of valve flap members is disposed within the central lumen and biased toward a closed position to occlude the central lumen, further comprising a biasing arm supporting each of the plurality of valve flap members, wherein the biasing arm is attached to and extends from the generally tubular stent and biases the valve flap members towards a closed position.

9. The implantable valvular prosthesis according to claim 8, wherein the biasing arm is formed from a portion of the generally tubular stent.

10. The implantable valvular prosthesis according to claim 8, wherein the plurality of valve flap members are attached to and extend from the generally tubular graft member.

11. The implantable valvular prosthesis according to claim 10, wherein the plurality of valve flap members are formed from a portion of the generally tubular graft member.

* * * * *

UNITED STATES PATENT AND TRADEMARK OFFICE
CERTIFICATE OF CORRECTION

PATENT NO.         : 7,195,641 B2
APPLICATION NO. : 10/120728
DATED                  : March 27, 2007
INVENTOR(S)       : Julio C. Palmaz et al.

It is certified that error appears in the above-identified patent and that said Letters Patent is hereby corrected as shown below:

Page 2 - U.S. PATENT DOCUMENTS - Column 2 - Line 23:
   Please delete "5,957,573 A 9/1999 Wedekind et al......623/1" and insert
   -- 5,997,573 A 12/1999 Quijano, et al.....623/1 --

Page 3 - OTHER DOCUMENTS - Column 2 - Line 7:
   Please delete "Heart" and insert -- Heartport --

Page 3 - OTHER DOCUMENTS - Column 2 - Line 18:
   Please delete "TiNiPd films" and insert -- TiNiPd and TiPd films --

Column 7 - Line 42:
   Please delete the second instance of "into the"

Column 8 - Line 10:
   Please add -- . -- after "member"

Column 10 - Line 10:
   Please delete "Robotewskyi" and insert -- Robotewski --

Column 10 - Line 54:
   Please delete "U.S. Pat. No. 5,891,507)" and insert -- (U.S. Pat. No. 5,891,507) --

Column 12 - Line 13:
   Please delete "a" and insert -- an --

Column 12 - Line 29:
   Please delete "an" and insert -- and --

Column 12 - Line 41:
   Please delete "manner"

Column 13 - Line 53:
   Please delete the second instance of "is a"

Column 15 - Line 16:
   Please delete "fabricated" and insert -- fabricate --

UNITED STATES PATENT AND TRADEMARK OFFICE
CERTIFICATE OF CORRECTION

PATENT NO. : 7,195,641 B2
APPLICATION NO. : 10/120728
DATED : March 27, 2007
INVENTOR(S) : Julio C. Palmaz et al.

It is certified that error appears in the above-identified patent and that said Letters Patent is hereby corrected as shown below:

Column 19 - Line 39:
　　Please delete "anchor section" and insert -- anchor sections --

Column 20 - Line 47:
　　Please delete "as prevent" and insert -- as to prevent --

Column 21 - Line 31:
　　Please delete "505. at" and insert -- 505 at --

Signed and Sealed this

Fourth Day of March, 2008

JON W. DUDAS
*Director of the United States Patent and Trademark Office*